United States Patent
Prasad

(10) Patent No.: US 10,952,985 B2
(45) Date of Patent: Mar. 23, 2021

(54) CHLOROGENIC ACID COMPOSITION FOR THE TREATMENT OF METABOLIC DISORDERS

(71) Applicant: Vidya Herbs, Inc., Fullerton, CA (US)

(72) Inventor: Kodimule Shyam Prasad, Bangalore (IN)

(73) Assignee: Vidya Herbs, Inc., Fullerton, CA (US)

( * ) Notice: Subject to any disclaimer, the term of this patent is extended or adjusted under 35 U.S.C. 154(b) by 188 days.

(21) Appl. No.: 16/158,002

(22) Filed: Oct. 11, 2018

(65) Prior Publication Data

US 2019/0111015 A1    Apr. 18, 2019

Related U.S. Application Data

(60) Provisional application No. 62/571,781, filed on Oct. 12, 2017.

(51) Int. Cl.
| | | |
|---|---|---|
| *A61K 31/216* | (2006.01) | |
| *A61K 36/28* | (2006.01) | |
| *A61P 3/06* | (2006.01) | |
| *A61P 3/10* | (2006.01) | |
| *A61P 3/04* | (2006.01) | |
| *A61K 9/00* | (2006.01) | |

(52) U.S. Cl.
CPC .......... *A61K 31/216* (2013.01); *A61K 9/0053* (2013.01); *A61K 36/28* (2013.01); *A61P 3/04* (2018.01); *A61P 3/06* (2018.01); *A61P 3/10* (2018.01)

(58) Field of Classification Search
CPC .... A61K 31/216; A61K 36/28; A61K 9/0053; A61P 3/04; A61P 3/06; A61P 3/10
See application file for complete search history.

(56) References Cited

U.S. PATENT DOCUMENTS 9,775,822 B2 * 10/2017 Prasad ...................... A61P 3/04

\* cited by examiner

*Primary Examiner* — Aaron J Kosar
(74) *Attorney, Agent, or Firm* — TMB Law; Timothy M. Brown

(57) ABSTRACT

A composition of chlorogenic acids and method of its use and manufacture in the treatment of metabolic disorders. The composition can be obtained from sunflower seed extract, including *Helianthus annulus* seeds.

13 Claims, 15 Drawing Sheets

CHLOROGENIC ACID COMPOSITION FOR THE TREATMENT OF METABOLIC DISORDERS

CROSS-REFERENCE TO RELATED APPLICATIONS

This application claims priority to Provisional Application No. 62/571,781 filed Oct. 12, 2017, the entire contents of which are incorporated herein by reference for all purposes.

FIELD OF THE INVENTION

The invention generally relates to the therapeutic compositions for treating metabolic disorders.

BACKGROUND

There are a variety of small molecule therapies available for treating metabolic disorders. For example, metformin has long been used for treating type 2 diabetes. Unfortunately, systemic exposure to metformin can pose a serious risk of lactic acidosis for several patient populations. Lactic acidosis is a potentially fatal metabolic complication that occurs when lactic acid levels increase in the bloodstream. Accordingly, metformin is contraindicated in people with any condition that could increase the risk of lactic acidosis, including kidney disorders, lung disease, and liver disease. According to prescribing information, heart failure, in particular, unstable or acute congestive heart failure, also increases risk of lactic acidosis with metformin. Thus, metformin remains unavailable to treat diabetes in patients with these contraindications.

Moreover, conventional metformin formulations often produce dose-limiting adverse gastrointestinal (GI) complications including diarrhea, nausea, vomiting, dizziness, headaches and dyspepsia. Accordingly, patient administration is generally titrated upward over a period of time to a maximum tolerated dose based in not insignificant part on any resulting patient-specific adverse GI effects. Extended-release formulations have been developed in the hopes of addressing side effects, but have not adequately resolved these problems.

Small molecule therapies are also available for treating obesity. Anti-obesity medication, or weight loss drugs, are pharmacological agents that reduce or control weight. These drugs alter one of the fundamental processes of the human body, weight regulation, by altering either appetite or absorption of calories. However, some anti-obesity drugs can have severe, even, lethal side effects, fen-phen being a famous example. Fen-phen was reported through the FDA to cause abnormal echocardiograms, heart valve problems, and rare valvular diseases. The side effects are often associated with the medication's mechanism of action. In general, stimulants carry a risk of high blood pressure, faster heart rate, palpitations, closed-angle glaucoma, drug addiction, restlessness, agitation, and insomnia. Another anti-obesity drug, orlistat, blocks absorption of dietary fats, and as a result may cause oily spotting bowel movements (steatorrhea), oily stools, stomach pain, and flatulence.

Dyslipidemias have been treated with statins, also known as HMG-CoA reductase inhibitors. Statins have been found to reduce cardiovascular disease (CVD) and mortality in those who are at high risk. The evidence is strong that statins are effective for treating CVD in the early stages of the disease (secondary prevention) and in those at elevated risk but without CVD (primary prevention). However, statins are not without their side effects, including muscle pain, increased risk of diabetes mellitus, and abnormalities in liver enzyme tests. Additionally, statins can have rare, but severe adverse effects, particularly muscle damage.

What is needed in the art therefore is a metabolic disorder therapy that avoids the side effects of conventional small molecule treatments. A further need is a metabolic disorder therapy that can be administered to patients where small molecule therapy is contraindicated.

SUMMARY OF THE INVENTION

The inventor surprisingly discovered a chlorogenic acid composition that can inhibit enzymes that are involved in number of metabolic disorders. In particular, the inventor observed that his composition inhibits alpha-glucosidase, alpha-amylase and lipase. It was further observed that the inventive composition activates AMPK and reduces PPAR and CEBP expression. Thus, the composition finds use in the treatment of metabolic disorders. The inventive composition provides an improvement over known small molecule metabolic disorder therapies by avoiding their harmful side effects. Moreover, the inventive composition can safely be administered to patients for whom small molecule therapy is contraindicated.

It is therefore an object of the invention to provide a composition for treating metabolic disorders, wherein the composition comprises a mixture of chlorogenic acids, wherein the mixture comprises by weight: 4.1±1.42% 3CQA; 28±4.65% 5CQA; 6.5±2.25 4 CQA; 0.84±0.26 4 CQA; 0.84±0.26 3,4 Di CQA; 1.23±0.34 3,5 Di CQA; and 1.85±0.42 4,5 Di CQA.

A further object of the invention is to provide a method for treating a metabolic disorder, wherein the method comprises administering to a patient in need thereof an effective amount of a composition comprising a mixture of chlorogenic acids, wherein the mixture comprises: 4.1±1.42% 3CQA; 28±4.65% 5CQA; 6.5±2.25 4 CQA; 0.84±0.26 4 CQA; 0.84±0.26 3,4 Di CQA; 1.23±0.34 3,5 Di CQA; and 1.85±0.42 4,5 Di CQA.

A still further object of the invention is to provide a method for making a chlorogenic acid composition for treating metabolic disorders, wherein the composition comprises: 4.1±1.42% 3CQA; 28±4.65% 5CQA; 6.5±2.25 4 CQA; 0.84±0.26 4 CQA; 0.84±0.26 3,4 Di CQA; 1.23±0.34 3,5 Di CQA; and 1.85±0.42 4,5 Di CQA.

These and other objects of the invention will be apparent to one skilled in the art in view of the following description and accompanying figures.

DEFINITIONS

Figure 1:
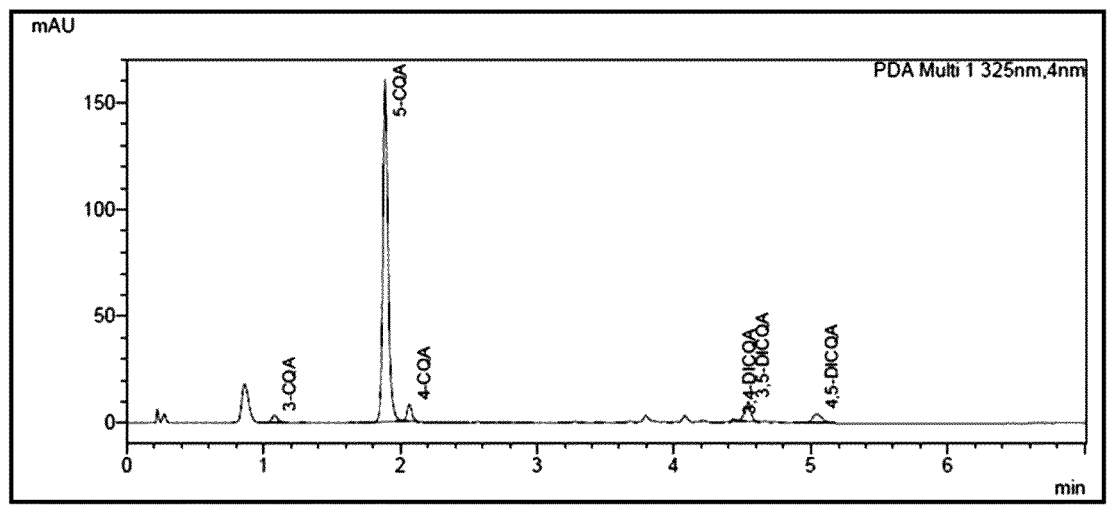
FIG. 1 shows an HPLC chromatogram analysis for an embodiment of the inventive composition.
Figure 2:
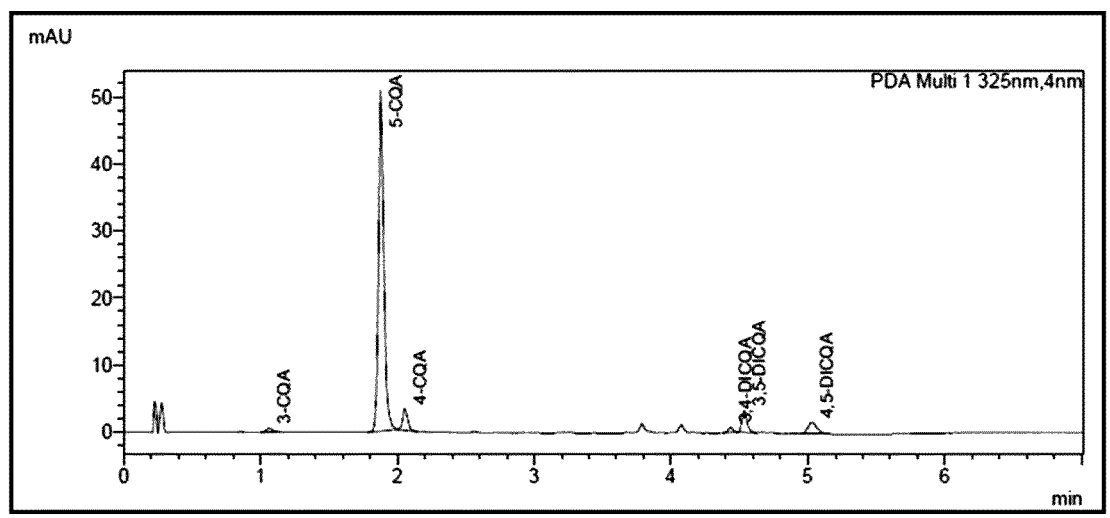
FIG. 2 shows an HPLC chromatogram analysis for an embodiment of the inventive composition.

As used herein, the term "about" means an amount that is equal to the stated value to which the term is applied, as well as amounts that are plus or minus 1%, 2%, 3%, 4%, 5%, 10%, or 20% of the stated value.

As used herein, and unless indicated otherwise, the term "diabetes" includes, but is not limited to, type 1 diabetes, type 2 diabetes, non-insulin dependent diabetes mellitus, diabetes insipidus. Diabetes can be accompanied by related complications including, for example, obesity and high cholesterol.

As used herein, the phrases "effective amount," "effective dose," and "therapeutically effective amount," refer to that amount of a therapeutic agent sufficient to ameliorate a disorder. For example, for the given parameter, a therapeutically effective amount will show an increase or decrease of therapeutic effect at least 5%, at least 10%, at least 15%, at least 20%, at least 25%, at least 40%, at least 50%, at least 60%, at least 75%, at least 80%, at least 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

As used herein, the term "hyperglycemia" and the phrase "high blood sugar," refer to a condition in which an excessive amount of glucose (e.g. greater than about a 125 mg/dL fasting plasma glucose level) circulates in the blood plasma.

As used herein, the term "increase" refers to any measurable increase in a parameter relative to control conditions.

As used herein, the phrase "metabolic disorder" includes, but is not limited to, being overweight, obesity, prediabetes, Polycystic Ovary Syndrome, dislipidemia or disorders of lipid metabolism (e.g. hyperlipidemia), hyperglycemic conditions, such as insulin-dependent (type 1) and insulin-independent (type 2) diabetes, as well as physiological conditions or disorders associated with or that result from the hyperglycemic condition.

As used herein, the terms "obese" and "obesity" refer to a subject having a body mass index of 30 or higher.

As used herein, the term "pre-diabetes" refers to symptoms of diabetes wherein the patient exhibits elevated glucose levels but the full onset of disorders associated with diabetes has not yet manifested itself.

As used herein, the term "reduce" refers to any measurable decrease in a parameter relative to control conditions.

As used herein, the terms "subject," "patient," "individual" and like terms are used interchangeably and refer to, except where indicated, mammals such as humans and non-human primates, as well as livestock and companion and laboratory research animals. The terms can refer to an individual that has been diagnosed, is currently following a therapeutic regimen, or is at risk of developing a metabolic disorder, e.g., due to family history, sedentary lifestyle, etc. Subjects include any of the aforementioned categories which have been used as a control.

As used herein, the terms "therapy," "treating," "treat," and "treatment" refer to the prevention or reduction in the severity or progression of symptoms in a patient having a targeted disorder. Treating can include administering to a subject a composition as disclosed herein for treating a disorder, such as a metabolic disorder.

DETAILED SPECIFICATION

The invention generally relates to a chlorogenic acid composition and methods for its use in therapeutic applications. More particularly, the invention relates to a chlorogenic acid composition and methods of its use and manufacture in the treatment of metabolic disorders.

Compositions

The inventor surprisingly discovered a chlorogenic acid composition that is capable of modulating enzymes involved in a number of metabolic disorders. The inventive composition can inhibit lipase, alpha-glucosidase, alpha-amylase, and combinations thereof. In addition, the inventive composition can decrease PPAR and EBP expression and activate AMPK.

In some embodiments the composition comprises a mixture having at least one chlorogenic acid. The mixture can comprise 3-O-Caffeoylquinic acid (3 CQA), 4-O-Caffeoylquinic acid (4 CQA), 5-O-Caffeoylquinic acid (5 CQA), 5-O-Feruloylquinic acid, 3,4-O-Dicaffeoylquinic acid (3,4 Di CQA), 3,5-O-Dicaffeoylquinic acid (3, 5 Di CQA), 4,5-O-Dicaffeoylquinic acid (4,5 Di CQA), or combinations thereof. The mixture can comprise chlorogenic acids selected from the group consisting of 3-CQA, 5-CQA, 4-CQA, 3,4-diCQA, 3,5-diCQA, 4,5-diCQA, or combinations thereof. The composition can comprise a mixture of chlorogenic acids that comprises 3-CQA, 5-CQA, 4-CQA, 3,4-diCQA, 3,5-diCQA, 4,5-diCQA, or combinations thereof. The composition can comprise a mixture of chlorogenic acids that comprises 3-CQA, 5-CQA, 4-CQA, 3,4-diCQA, 3,5-diCQA, 4,5-diCQA, or combinations thereof, wherein the composition is free of any other chlorogenic acids.

In some aspects of the invention, the composition can comprise a mixture of chlorogenic acids, each present in a weight-to-weight percentage relative to the other components of the mixture. The mixture can comprise 4.0±2.0 w/w % 3-CQA, 28.0±5.0 w/w % 5-CQA, 7.0±3.0 w/w % 4-CQA, 1.0±0.50 w/w % 3,4-diCQA, 1.5±0.5 w/w % 3,5-diCQA, and 2.0±0.5 w/w % 4,5-diCQA. In another embodiment, the mixture can comprise 4.1±1.42 w/w % 3-CQA, 28±4.65 w/w % 5-CQA, 6.5±2.25 w/w % 4-CQA, 0.84±0.26 w/w % 3,4-diCQA, 1.23±0.34 w/w % 3,5-diCQA, and 1.85±0.42 w/w % 4,5-diCQA.

The total chlorogenic acid content of the mixture can range between about 20% and about 60%. The total chlorogenic acid content can be about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the mixture. The mixture can have a total chlorogenic acid content of about 42.50%. The mixture can have a total chlorogenic acid content of 42.50±2.5 w/w %. The total chlorogenic acid content can be constituted from one or more of 3 CQA, 5 CQA, 4 CQA, 3,4 Di CQA, 3,5 Di CQA, 4,5 Di CQA.

In one non-limiting embodiment, the mixture comprises 4.0±2.0 w/w % 3-CQA, 28.0±5.0 w/w % 5-CQA, 7.0±3.0 w/w % 4-CQA, 1.0±0.50 w/w % 3,4-diCQA, 1.5±0.5 w/w % 3,5-diCQA, and 2.0±0.5 w/w % 4,5-diCQA, wherein the mixture has a total chlorogenic acid content of about 42.50%.

In another non-limiting embodiment, the composition comprises a mixture of chlorogenic acids, wherein the mixture comprises 4.1±1.42 w/w % 3-CQA, 28±4.65 w/w % 5-CQA, 6.5±2.25 w/w % 4-CQA, 0.84±0.26 w/w % 3,4-diCQA, 1.23±0.34 w/w % 3,5-diCQA, and 1.85±0.42 w/w % 4,5-diCQA, wherein the mixture has a total chlorogenic acid content of 42.50±2.5 w/w %.

In some aspects of the invention, the mixture of chlorogenic acids can comprise one or more polyphenols. The mixture can comprise between about 20% and about 60% polyphenols. The mixture can comprise, by weight, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% polyphenols. In one non-limiting embodiment, the mixture comprises 47.50±2.5 w/w % polyphenols.

In some aspects of the invention, the mixture of chlorogenic acids is obtained from a plant extract. Such extracts can be obtained from any plant material capable of providing a mixture of chlorogenic acids as described herein. The plant material can be seeds, leaves, stems, fruit, stalks, flowers, pollen, roots, or combinations thereof. In one non-limiting embodiment, the plant material is from the sunflower plant, including, but not limited to *Helianthus annuus*. The extract can be obtained from sunflowers seeds, including, but not limited to *Helianthus annuus* seeds.

Extracts for use with the invention can be obtained from solvent extraction. The solvent can be an aqueous solvent. The solvent can be an alcohol-based solvent, including, but not limited to ethanol, methanol or a combination thereof. The extract can be obtained by supercritical fluid extraction. The supercritical fluid extraction solvent can be, but is not necessarily limited to, carbon dioxide.

In some aspects of the invention, the composition can comprise an excipient, a carrier, or a combination thereof. The excipient can be selected on the basis of compatibility with the mixture and the properties of the desired dosage form. The excipient can be selected from the group consisting of binders, fillers, bulking agents, flow aids/glidents, disintegrants, lubricants, stabilizers, surfactants, and combinations thereof. Suitable excipients and carriers for use with the composition include, but are not limited to, those disclosed in: Remington: The Science and Practice of Pharmacy, 19$^{th}$ Ed (Easton, Pa.: Mack Publishing Company, 1995); Hoover, John E., Remington's Pharmaceutical Sciences, (Easton, Pa.: Mack Publishing Co 1975); Liberman, H. A. and Lachman, L., Eds., Pharmaceutical Dosage Forms (New York, N.Y.: Marcel Decker 1980); and Pharmaceutical Dosage Forms and Drug Delivery Systems, Seventh Ed (Lippincott Williams & Wilkins 1999). The entire contents of these publications are incorporated herein by reference for all purposes.

In at least one embodiment, the composition may further employ controlled, sustained, or extended release formulations known collectively as "modified release" formulations. The composition can be administered by modified release systems or by delivery devices that are well known to those of ordinary skill in the art. Examples include, but are not limited to, those described in U.S. Pat. Nos. 3,845,770;

3,916,899; 3,536,809; 3,598,123; 4,008,719; 5,674,533; 5,059,595; 5,591,767; 5,120,548; 5,073,543; 5,639,476; 5,354,556; and 5,733,566. Dosage forms for the composition can be used to provide modified release of one or more active ingredients using, for example, hydropropylmethyl cellulose, other polymer matrices, gels, permeable membranes, osmotic systems, multilayer coatings, microparticles, liposomes, microspheres, or a combination thereof. Suitable modified release formulations known to those of ordinary skill in the art, including those described herein, can be readily selected for use with the composition of the invention. The composition can be in the form of a powder, liquid, pill, tablet, pellet, capsule, thin film, solution, spray, syrup, linctus, lozenge, pastille, chewing gum, paste, vapor, suspension, emulsion, ointment, cream, lotion, liniment, gel, drop, topical patch, buccal patch, bead, gummy, gel, sol, or injection. The composition can be formulated for oral administration. The composition can comprise vitamins, minerals, extracts, amino acids, protein, carbohydrates, lipids, excipients, caffeine, flavorings, sweeteners, preservatives, or combinations thereof.

Methods

In some aspects, the invention provides a method for treating a metabolic disorder in a patient in need thereof. Such methods can be practiced by administering to the patient an effective amount of the composition, wherein administering the composition treats the metabolic disorder in the patient.

Metabolic disorders treatable by the methods of the invention include, but are not limited to, being overweight, obesity, prediabetes, Polycystic Ovary Syndrome, dislipidemia or disorders of lipid metabolism (e.g. hyperlipidemia), as well as hyperglycemic conditions, such as insulin-dependent (type 1) or -independent (type 2) diabetes, as well as physiological conditions or disorders associated with or that result from the hyperglycemic condition. Thus, hyperglycemic conditions treatable by a method of the invention include a histopathological change associated with chronic or acute hyperglycemia (e.g., diabetes). Particular examples include degeneration of the pancreas (beta cell destruction), kidney tubule calcification, degeneration of liver, eye damage (e.g. diabetic retinopathy), diabetic foot, ulcerations in mucosa such as mouth and gums, excess bleeding, delayed blood coagulation or wound healing and increased risk of coronary heart disease, stroke, peripheral vascular disease, dyslipidemia, hypertension, and obesity.

In some aspects of the invention, administering the composition treats diabetes. Administering the composition can treat a complication associated with diabetes including, but not limited to, retinopathy (i.e., blindness); neuropathy (i.e., nerve damage) which leads to foot ulcers, gangrene, and amputations; kidney damage, which leads to dialysis; and cardiovascular disease. Administering the composition to a patient with diabetes or prediabetes can reduce total blood glucose content, reduce blood insulin, reduce the blood insulin to blood glucose ratio, increase insulin sensitivity, or a combination thereof. Administering the composition can similarly improve a patient's serum lipid profile.

A patient treated for diabetes with the inventive composition can be ineligible for treatment with metformin. The patient can be ineligible for treatment with metformin due to a risk of developing lactic acidosis due to kidney disorders (e.g. renal disease, renal impairment or renal dysfunction), dehydration, unstable or acute congestive heart failure, acute or chronic metabolic acidosis, hereditary galactose intolerance, lung disease, liver disease or heart failure (e.g. unstable or acute congestive heart failure). The patient for diabetes can be an elderly patient ineligible for metformin therapy due to reduced renal function. The patient treated for diabetes can be ineligible for metformin therapy due to one or more metformin side effects including diarrhea, nausea, vomiting, dizziness, headaches, dyspepsia, or a combination thereof.

Administering the composition to a patient can produce one or more therapeutic effects. The composition can reduce blood glucose, increase insulin sensitivity, reduce body weight, reduce percent body fat, increase percent lean mass, reduce serum cholesterol, reduce low density lipoprotein, reduce very low density lipoprotein, reduce serum triglycerides, increase high density lipoprotein, or combinations thereof. In some aspects of the invention, administering the composition to the patient modulates glucose metabolism in the patient. Such alteration can include any measurable change in at least one aspect of glucose metabolism including, but not limited to, total blood glucose content, blood insulin, the blood insulin to blood glucose ratio, insulin sensitivity, oxygen consumption, or combinations thereof.

In some aspects of the invention, the invention provides a method of treating dyslipidemia (e.g. hyperlipidemia). In such methods, the patient can have elevated blood levels of total lipid content, HDL cholesterol, LDL cholesterol, VLDL cholesterol, triglyceride, Lp(a), apo A-I, apoE, non-esterified fatty acids, or combinations thereof. Administering the composition to such patients can reduce one or more of these levels, as well as improve the ratio of HDL to LDL in such patients.

In some aspects, the invention provides a method of treating obesity, Accordingly, administering the composition to the patient can reduce body weight, reduce percent body fat, increase percent lean mass, or combinations thereof. Administering the composition can treat a complication associated with obesity. Such complications include, but are not limited to, hypercholesterolemia, hypertension, dyslipidemia (for example, high total cholesterol or high levels of triglycerides), type 2 diabetes, coronary heart disease, stroke, gallbladder disease, osteoarthritis, sleep apnea and respiratory problems, and some cancers (endometrial, breast, and colon).

One aspect of the invention concerns the dosage of the composition. The composition can be administered at a dose of between about 5 mg/day to about 500 mg/day. The composition can be administered at a dose between about 20 mg/day to about 1 mg/day. The composition of the invention can be administered at a dose of about 20 mg/day, about 21 mg/day, about 22 mg/day, about 23 mg/day, about 24 mg/day, about 25 mg/day, about 26 mg/day, about 27 mg/day, about 27 mg/day, about 28 mg/day, about 29 mg/day, about 30 mg/day, about 31 mg/day, about 32 mg/day, about 33 mg/day, about 34 mg/day, about 35 mg/day, about 40 mg/day, about 45 mg/day, about 50 mg/day, about 100 mg/day, about 150 mg/day, about 200 mg/day, about 250 mg/day, about 300 mg/day, about 350 mg/day, about 400 mg/day, about 450 mg/day, or about 500 mg/day, as well as any dosage intervening these specifically disclosed amounts. The composition can be administered at a dosage of between about 400 mg/day to about 500 mg/day, between about 300 mg/day to about 400 mg/day, between about 200 mg/day to about 300 mg/day, between about 100 mg/day to about 200 mg/day, between about 100 mg/day to about 200 mg/day, or about 20 mg/day to about 100 mg/day. It is contemplated that the composition can be administered at any dosage that intervenes the dosages called out in this specification. The composition can be administered systemically. The composition can be administered to the patient topically, orally, buccally, sub-lingually, parenterally, intravenously, intranasally, intravaginally, rectally, or by inhalation.

In some aspects, the dosage of the composition is determined by the body weight of the patient. The composition can be administered between about 5 mg/kg b.w. and about 500 mg/kg b.w. The composition can be administered at about 5 mg/kg b.w., about 10 mg/kg b.w., about 20 mg/kg b.w., about 30 mg/kg b.w., about 40 mg/kg b.w., about 50 mg/kg b.w., about 60 mg/kg b.w., about 70 mg/kg b.w., about 80 mg/kg b.w., about 100 mg/kg b.w., about 120 mg/kg b.w., about 140 mg/kg b.w., about 160 mg/kg b.w., about 180 mg/kg b.w., about 200 mg/kg b.w., about 220 mg/kg b.w., about 240 mg/kg b.w., about 260 mg/kg b.w., about 280 mg/kg b.w., about 300 mg/kg b.w., about 320 mg/kg b.w., about 340 mg/kg b.w., about 360 mg/kg b.w., about 380 mg/kg b.w., about 400 mg/kg b.w., about 420 mg/kg b.w., about 440 mg/kg b.w., about 460 mg/kg b.w., about 480 mg/kg b.w., or about 500 mg/kg b.w. In one non-limiting embodiment of the invention, the composition is administered at about 150 mg/kg b.w. The composition can be administered, one, two, three, four, five or more times. The composition can be administered daily, weekly, monthly, or combinations thereof. The composition can be administered one, two, three, four, five, six or more times per day, per week, or per month. One skilled in the art will appreciate that the administration of the composition can be adjusted according to the patient's response to the treatment and the therapeutic outcome desired by the patient or attending physician.

The present disclosure is further described in the light of the following non-limiting examples which are set forth for illustration purpose only and not to be construed for limiting the scope of the specification.

Example 1—Preparation of Sunflower Material 100 kg of sunflower seed powder was taken into a cleaned vertical 1.0 KL extractor. The bottom of the extractor comprised perforated plate on which filtration cloth was fixed. The bottom of the extractor was connected to a transfer pump input and output of the transfer pump was connected to T bend. One end was connected to extractor top for circulation of extraction mass while extraction period and other end of T bend were connected to receiver tank.

The above mentioned mass was extracted with 7-8 bed volumes of demineralized water. Extraction was continued at 80-85° C. temperature about 7-8 hrs with continuous circulation of extract with transfer pump. After completion of extraction, the extract was filtered through a 5 micron SS candle filter and clear extract was collected in a receiver tank. The bed was re-extracted by adding 5-6 bed volumes of demineralized water 3 more times at 80-85° C. temperature about 7-8 hrs and filtered through a 5 micron SS candle filter. All the extracts were collected in a receiver tank and the combined extracts were concentrated in a reactor under vacuum at 80-85° C. until the extract moss TDS reached 25-30 w/v % and was cooled to room temperature. The oily layer was separated and the aqueous layer collected.

The above aqueous layer was taken and the solution was adjusted to pH to 2-2.2 with dilute sulfuric acid and stirred well about 15 minutes. The solution was filtered through celite bed to make it into clear solution. The solution was loaded into a macroporus XAD-16N (Rohm & Haas Company) resin column at the rate of 2-3 bed volumes/hour. The resin bed was washed with 4-6 bed volumes of demineralized water at the rate of 2-3 bed volumes/hour. Further it was eluted with 3-4 bed volumes of 70-75 v/v % ethyl alcohol at the rate of 2-3 bed volumes/hour. The eluent was concentrated in a reactor at 75-80° C. until free from ethyl alcohol. The extract mass was dissolved into demineralized water until the TDS reached 25-30 w/v %. The extract was spray dried at 185-190° C. The yield of the extract was about 2.8±0.2 w/w %.

The extract obtained by the method of Example 1 was used in the following examples.

Example 2—Spectrophotometric and HPLC Derivation

The composition obtained under Example 1 was subjected to phytochemical derivation through spectrophotometric and HPLC estimations.

A. Derivation of Polyphenol Content by Folin-Ciocalteous Method

Standard Preparation 100 mg of STD (99.9% pure) was dissolved in 100 ml of volumetric flask by using 50% methanol solution (1000 ppm Chlorogenic acid stock standard). From this a 1000 ppm stock standards were prepared at 30 ppm, 60 ppm, 90 ppm, 120 ppm, 150 ppm, and 180 ppm by dilution using 50% methanol solution.

Sample Preparation 15-20 mg of the preparation from Example 1 was placed into 100 ml of volumetric flask, about 50 ml of 50% methanol solution was added and the mixture sonicated for 5 mins, then diluted to 100 ml with 50% methanol, then further diluted to 5.0 ml of above solution to 10 ml using 50% methanol.

Prepared a series of test tubes (one for blank, each STDs and samples) each containing 15 ml of 50% methanol solution+1 ml of Folin-Ciocalteus reagent followed by 1.0 ml of standard, sample or 50% methanol solution. Allowed the above solutions at room temperature for 10 mins. Added 3.0 ml of 20% $Na_2CO_3$ solution to each tube, mixed well. Placed tubes in a water bath at 40° C. for 20 minutes. Immediately placed tubes into an ice bath upon removal from water bath for 2 minutes. Removed the tubes and allowed to come to room temperature. Measured the absorbance of blank, standards and samples at 755 nm. (Table 1).

Calculation $$\% \text{ Total Polyphenols} = \frac{\frac{A_{sample} - b}{m} \times V \times DF \times 100}{W_{sample} \times 1000}$$

Where,
V—Original volume 50 ml
$W_{sample}$—sample weight in grams
DF—dilution factor
$A_{sample}$—sample absorbance
m, b-Coefficients of standard curve Slope and y-intercept.

TABLE 1

Estimation of Total Polyphenols

| S.N. | Phyto-constituents | Analysis Method | Sunflower seed (Raw material) (%) | Composition |
|---|---|---|---|---|
| 1 | Total polyphenols | Spectrophotometric | 1.80 ± 0.40 w/w %. | 47.50 ± 2.5 w/w % |

Results

Percentage of total polyphenols in the composition (47.50±2.5 w/w %) was higher as compared to raw material of sunflower seed extract (1.80±0.40 w/w %).

B. Derivation of Chlorogenic Acid Content by HPCL

Analytical Parameters:
Column: XB-C18 100 A, 2.6 μm, 50×2.1 mm Phenomenex. (Kinetex)
Pump: Nexera X2, LC-30AD Shimadzu
Detector: SPD-M20A PDA
Wave length: 325 nm
Flow rate: 0.6 mL/min
Volume of injection: 1 μL
Run time: 7 min.
Mobile phase: 0.1% Formic acid in HPLC grade water: Acetonitrile
Reference standard: Chlorogenic acid—98%
Gradient

| Time | B concentration (Acetonitrile) |
| --- | --- |
| 0.01 | 5 |
| 4.0 | 20 |
| 5.0 | 5 |
| 7.0 | Stop |

Standard Preparation 15-20 mg of standard chlorogenic acid (98%) was weighed into a 50 ml standard flask, add 30 ml 70% methanol and sonicated about 10 minutes. Made up to the mark with same solvent. Pipetted out 10 mL of the above solution to 50 ml standard flask and made up to the mark with same solvent and sonicated about 10 minutes.

Sample Preparation 40-50 mg of sample was weighed into 50 ml standard flask, added 30 ml 70% methanol and sonicated about 10 minutes. Made up to the mark with same solvent. Pipetted out 10 mL of the above solution to 50 ml standard flask and made up to the mark with same solvent and sonicated about 10 minutes.

Sample Preparation 1000-1500 mg of composition was weighed into 100 ml RB flask, added 40 ml 70% methanol. Refluxed about half an hour and cooled. Filtered in a 100 ml standard flask. Repeated extraction 2 more times with 30 ml of 70% methanol and filtered. Made up the volume to 100 ml using 70% methanol and sonicated about 10 minutes.

Calculation $$\% \text{ of chlorogenic acids} = \frac{\text{Peak area of the sample} \times Conc. \text{ of the } STD \times \text{purity of the } STD}{\text{Peak area of the standard} \times Conc. \text{ of the sample}}$$

TABLE 2

Percentage of Total Chlorogenic Acid

| S.N. | Phyto-constituents | Analysis Method | Sunflower seed (Raw material) (%) | Composition (%) |
| --- | --- | --- | --- | --- |
| 1 | Chlorogenic acids | HPLC | 1.65 ± 0.25 w/w %. | 42.50 ± 2.5 w/w % |

TABLE 3

Chlorogenic Acid Isomers

| S.N. | Chlorogenic acid isomers | Sunflower seed (%) | Composition (%) |
| --- | --- | --- | --- |
| 1 | 3 CQA | 0.04 ± 0.02 w/w % | 4.1 ± 1.42 w/w % |
| 2 | 5 CQA | 1.35 ± 0.25 w/w % | 28 ± 4.65 w/w % |
| 3 | 4 CQA | 0.08 ± 0.04 w/w % | 6.5 ± 2.25 w/w % |
| 4 | 3,4 Di CQA | 0.0068 ± 0.0001 w/w % | 0.84 ± 0.26 w/w % |
| 5 | 3,5 Di CQA | 0.1 ± 0.04 w/w % | 1.23 ± 0.34 w/w % |
| 6 | 4,5 Di CQA | 0.08 ± 0.02 w/w % | 1.85 ± 0.42 w/w % |

Results

Percentage of total chlorogenic acid in the composition from Example 1 (42.50±2.5 w/w %) was higher as compared to raw material of sunflower seed extract (1.65±0.25 w/w %) (Tables 2 and 3).

C. Chlorogenic Acid Content of the Composition by LCMS/MS

Analytical Parameters
Column: XB-C18 Phenomenex (Kinetex), 100 A, 2.6 μm & 50×2.1 mm
Pump: Nexera X2, LC-30AD Shimadzu
Detector: SPD-M20A PDA and LCMS/MS 8040
Wavelength: 325 nm
Flow rate: 0.6 mL/min
Volume of injection: 1 μL
Run time: 7 min.
Mobile phase (A: B): Acetonitrile: 0.1% Formic acid in LCMS grade water
DL Temp.: 4000 C
Nebulizing gas flow: 3 L/min.
Heat block temp: 5000 C
Drying gas flow: 15 L/min.
MS detection: ESI −ve mode, SIM at m/z 353 and 515, MRM at m/z 191,178 and 353
Gradient

| Time | B concentration (Acetonitrile) |
| --- | --- |
| 0.01 | 5 |
| 4.0 | 20 |
| 5.0 | 5 |
| 7.0 | Stop |

Sample Preparation 40-50 mg of sample was weighed into 50 ml standard flask, 30 ml 70% methanol (LCMS) was added and sonicated about 10 minutes. Made up to the mark with same solvent. Pipetted out 10 mL of the above solution to 50 ml standard flask and made up to the mark with same solvent and sonicated about 10 minutes.

Raw Material Sample Preparation 1000-1500 mg of raw material powder was weighted into 100 ml RB flask, add 40 ml 70% methanol (LCMS). Refluxed about half an hour and cooled. Filtered in a 100 ml standard flask. Repeated extraction 2 more times with 30 ml of 70% methanol and filter. Made up the volume to 100 ml using 70% methanol and sonicated about 10 minutes.

Results

Figure 3:
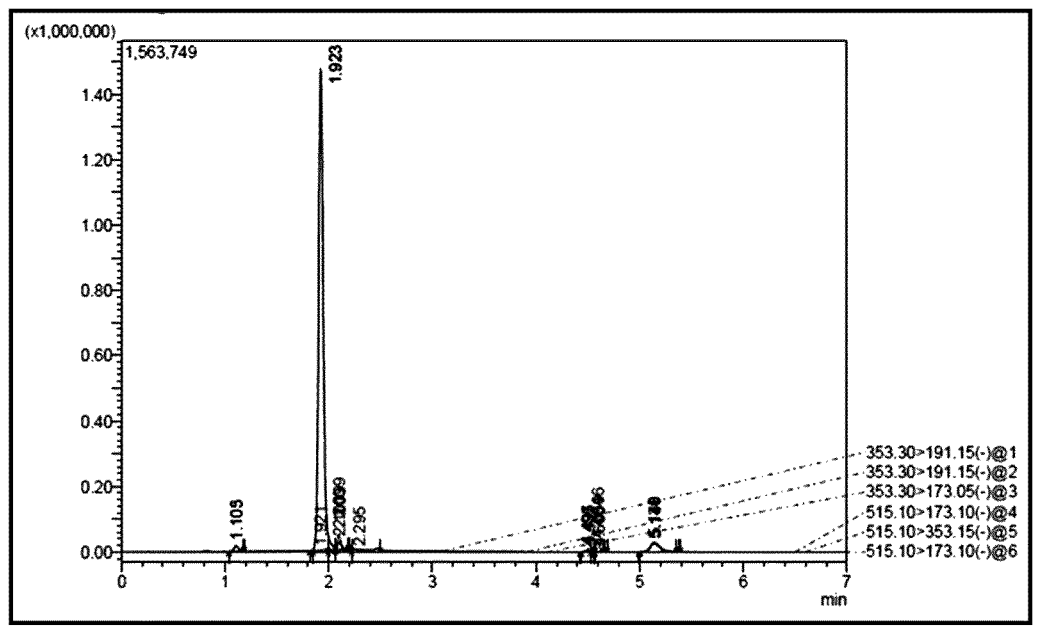
FIG. 3 shows an LCMS/MS chromatogram for an embodiment of the inventive composition.
Figure 4:
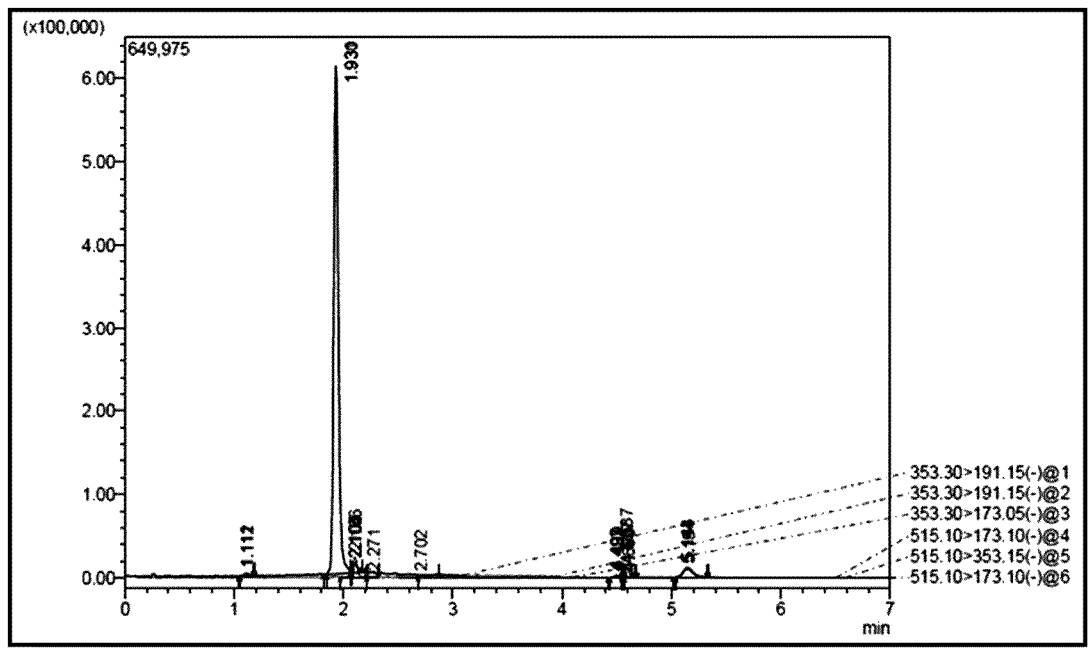
FIG. 4 shows an LCMS/MS chromatogram for an embodiment of the inventive composition.

The composition of sunflower seed (raw material) and the composition from Example 1 was established by the LC-MS/MS method. (FIG. 3 and FIG. 4)

Example 3—Toxicity Study

The Ames test is widely used in the determination of possible gene mutations by various agents. A positive response in any single bacterial strain either with or without metabolic activation is sufficient to designate a substance as an antimutagen. It is estimated that 90% of all carcinogens also are mutagens, and with this figure in mind, Bruce Ames and his colleagues developed a test in the 1970s that uses special bacteria that are very sensitive to mutagenic agents. The Food and Drug Administration (FDA) now uses the Ames test to screen many chemicals rapidly and inexpensively. Those few chemicals that appear to be mutagenic by the Ames test are tested further in animals to assess their ability to cause cancer.

The *Salmonella* mutagenicity test was specifically designed to detect chemically induced mutagenesis both in presence and absence of metabolic activation. This assay helps to identify substances that can produce genetic damage that leads to gene mutations. Mutant strains of *Salmonella typhimurium* that are used in AMES assay cannot synthesize histidine, and are very susceptible to additional mutations because they lack the normal repair mechanisms found in bacteria. These mutant strains are more permeable than wild-type bacteria to external chemicals, including potential mutagens. In order for these cells to survive on a plate that lacks histidine, they must regain the ability to synthesize histidine by undergoing another mutation that corrects the original mutation that prevented the production of the missing enzyme. This type of mutation is known as a back mutation, or reversion, because this second mutation returns the mutant to the wild-type (prototrophic) phenotype. This reversion can happen spontaneously due to incorrect DNA replication or as the result of a mutagen.

In this assay specific strains of the bacteria *Salmonella typhimurium* (TA 98, TA 100) were used to detect mutations. These strains of *S. typhimurium* used are known as auxotrophs and will not grow unless the nutrient is supplied in growth media. In order for these cells to survive on a plate that lacks histidine, they must regain the ability to synthesize histidine by undergoing another mutation that corrects the original mutation that prevented the production of the missing enzyme. The number of colonies that revert and grow (in presence and absence of metabolic activating system) is proportional to the mutagenicity of the test compound.

Procedure

Animal Treatment

The *S. typhimurium* strains used in the experiments were: TA 100 and TA98. Liver cytosolic fractions were prepared from young adult male Wistar rats. According to INVITTOX Protocol (Borenfreund and Puemer, 1990), animals were sacrificed after 5 days of receiving daily i.p. injections of sodium Phenobarbital at 30 mg/kg (day 1) and 60 mg/kg (days 2-5). On the third day, 80 mg/kg of 5, 6 b-naphtoflavone were also administered. The 9000 g liver supernatant (S9) was split into 1 mL aliquots, frozen and stored at −80° C.

Assay

The standard pre-incubation method in the presence and absence of S9 was performed according Maron and Ames, 1983. For this study, the composition of Example 1 was prepared in DMSO at stock concentration of 10 mg/mL and it was added to the cultures at 1, 2 & 3 mg/plate. Negative (vehicle-DMSO) and positive controls 4-Nitro-Phenylene diamine and EtBr were included.

Briefly, 0.5 ml of S9 mix (or 0.1 M phosphate buffer, pH 7.4), 0.1 ml of bacterial culture and 0.1 ml of test solution (or solvent) were added to each tube. The mixture was vortexed, and then allowed to incubate at 37° C. with shaking for 30 min. Following this pre-incubation period, 2.0 ml of molten top agar (45° C.) supplemented with histidine and biotin (0.5 mM) was dispensed into the tubes, which were immediately vortexed and the contents poured onto the surface of bottom minimal glucose agar Vogel and Bonner, 1956. When the agar overlay had solidified, the plates were inverted and placed in a 37° C. incubator. After incubation for approximately 48 h the revertant colonies were counted.

Results

Figure 5:
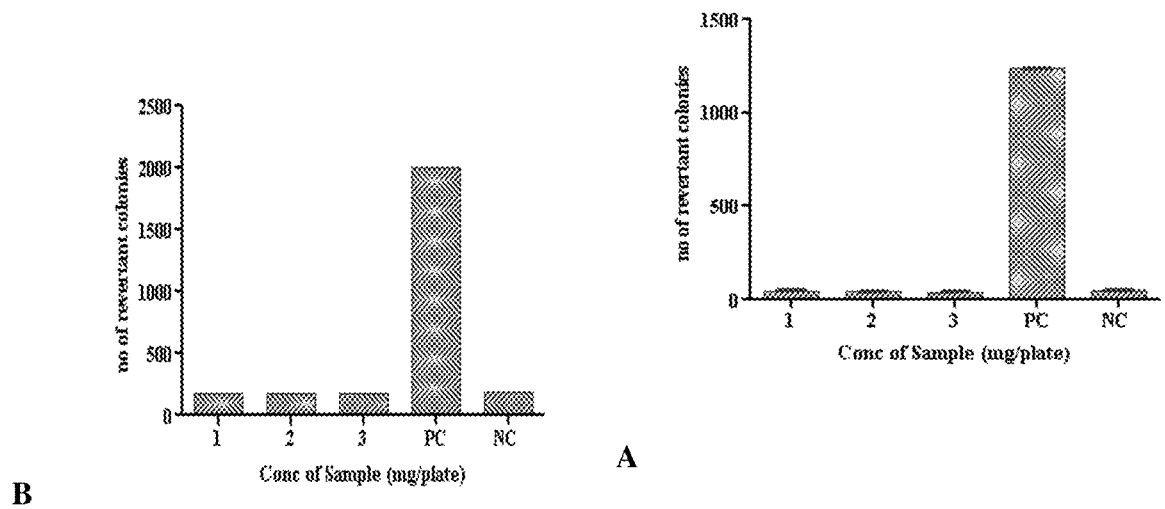
FIG. 5 shows mutagenic activity of an embodiment of the inventive composition against (A) TA 100 and (B) TA98 in the absence of S9 fraction.
Figure 6:
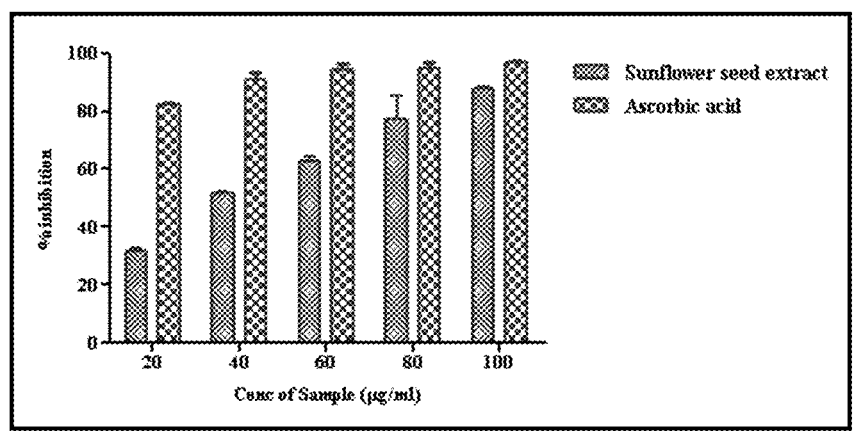
FIG. 6 shows inhibition of DPPH radical activity by an embodiment of the inventive composition.

From the above results, the strains of *S. typhimurium* viz., TA98 & TA100 exposed to different concentrations of the composition did not show a twofold or greater increase in the mean number of revertants as compared to the negative control group as given in Table 4. All strains used in the study exhibited a marked increase (>10-fold) in the number of revertants when treated with positive control agents. The results confirmed the sensitivity of the test strains to mutagens and thus the validity of the assay. The results indicated that the mean number of histidine revertants in the treatment groups were comparable to the mean number of revertants in the negative control group in the *S. typhimurium* tester strains viz., TA98 & TA100 both in the absence and the presence of metabolic activation. The composition up to 5 mg/plate in the presence and absence of metabolic activation was found to be non-mutagenic to *S. typhimurium* tester strains (Table 4, FIG. 5, and FIG. 6).

TABLE 4

Mutagenic Activity

| Conc. | Revertant colonies/plate (Mean n = 2 ± S.D.) | | | |
|---|---|---|---|---|
| | TA 100 | | TA 98 | |
| (mg/plate) | −s9 | +s9 | −s9 | +s9 |
| NC (DMSO) | 181.0 ± 5.65 | 184 ± 2.8 | 41.5 ± 2.12 | 49.0 ± 1.4 |
| 2 | 179.5 ± 0.7 | 180.5 ± 4.9 | 39.5 ± 0.7 | 45.5 ± 2.1 |
| 4 | 170.5 ± 2.1 | 179.0 ± 5.6 | 40.5 ± 0.7 | 44.0 ± 7.0 |
| 5 | 167.0 ± 2.8 | 182 ± 2.8 | 41.0 ± 1.4 | 39.0 ± 2.8 |
| PC SA | 2345.5 ± 6.3 | NA | NA | NA |
| PC NOP | NA | NA | 610 ± 11.3 | NA |
| PC 2AF | NA | 2737 ± 4.9 | NA | 1560 ± 3.53 |

Key:
S.D. = Standard deviation,
NC = Negative control,
DMSO = Dimethyl sulfoxide,
PC = Positive control,
NOP = 4-Nitro-O-phenylene diamine,
SA = Sodium azide,
2AAF = 2-aminoanthracene,
NA = Not Applicable,
n = No. of replicates Example 4—In-Vitro Anti-Oxidant Activities

4.1. DPPH Radical Scavenging Assay

The free radical scavenging capacity of the test sample was determined using DPPH scavenging assay. DPPH solution was prepared in 95% methanol. Freshly prepared DPPH solution was taken in test tubes and different concentration of test samples were added and incubated for 20 min. The absorbance was read at 517 nm using a spectrophotometer. Blank was prepared containing the same volume of reaction mixture without any tested samples. The percentage of scavenging was calculated using the formula:

$$\% \text{ Scavenging} = Ac-As/Ac \times 100$$

Where $A_C$ was the absorbance of the control (blank) and $A_S$ was the absorbance in the presence of the composition (Braca et al., 2001).

Results

Figure 7:
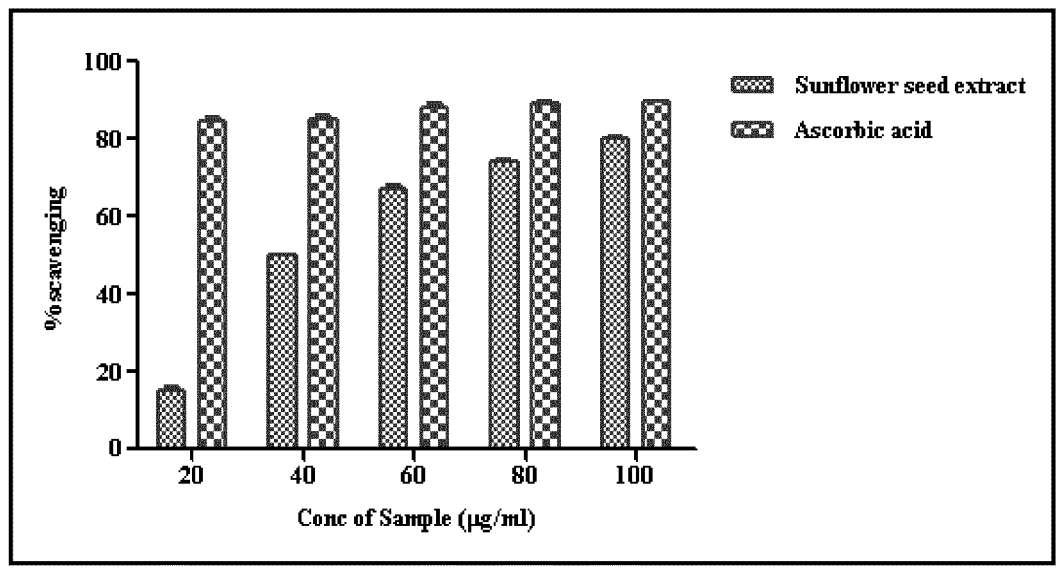
FIG. 7 shows superoxide anion scavenging activity of an embodiment of the inventive composition.

Table 5 shows the concentration dependent increase in DPPH radical scavenging activity of the composition, compared with ascorbic acid. It was observed that the composition had maximum activity of 87.88% at concentration of 100 μg/ml, which was comparable with ascorbic acid (96.71%) (Table 5, FIG. 7).

TABLE 5

DPPH Scavenging Activity

| Conc. in μg/ml | Composition | | Ascorbic acid | |
|---|---|---|---|---|
| | Absorbance @517 nm | % inhibition | Absorbance @517 nm | % inhibition |
| Blank | 2.281 | | 0.274 | |
| 20 | 1.556 | 31.78 | 0.046 | 83.21 |
| 40 | 1.097 | 51.88 | 0.025 | 90.88 |
| 60 | 0.855 | 62.52 | 0.015 | 94.53 |
| 80 | 0.514 | 77.42 | 0.014 | 94.89 |
| 100 | 0.277 | 87.88 | 0.009 | 96.72 |

4.2. Superoxide Anion Scavenging Activity

Superoxide anion scavenging activity of the composition of Example 1 was measured according to the method of Nishimiki et al., 1972. Prepared all the solutions in this experiment using phosphate buffer (pH 7.4). Added 1 ml of NBT (156 μM), 1 ml of NADH (468 μM) and 3 ml of test samples to all test tubes. The reaction was started by adding 100 ml of PMS (60 μM) and incubated the mixture at 25° C. for 5 min followed by measurement of absorbance at 560 nm. The percentage of scavenging was calculated using formula:

$$\% \text{ Scavenging} = Ac-As/Ac \times 100$$

Where $A_C$ was the absorbance of the control (blank) and $A_S$ was the absorbance in the presence of the composition.

Results

Figure 8:
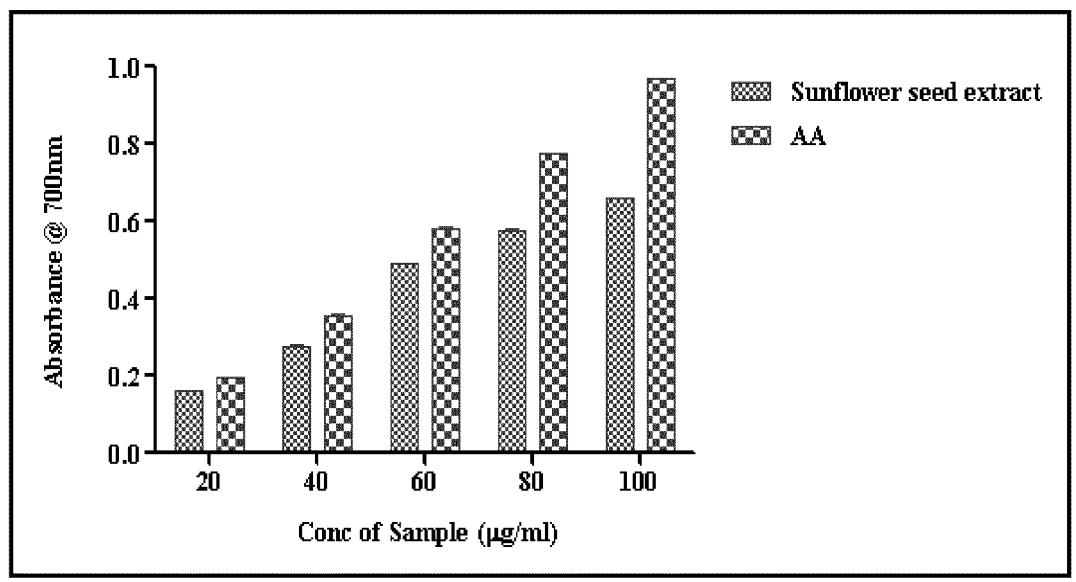
FIG. 8 shows reducing power activity of an embodiment of the inventive composition.

The superoxide radicals can be measured by its ability to reduce NBT. The ability of the composition and the reference compound ascorbic acid to quench superoxide radicals from reaction mixture was reflected in the decrease of the absorbance a 560 nm. From the results (FIG. 8 and Table 6), the composition is a potent scavenger of superoxide radical.

TABLE 6

Superoxide Scavenging Activity

| Conc. in μg/ml | Composition | | Ascorbic acid | |
|---|---|---|---|---|
| | Absorbance @560 nm | % inhibition | Absorbance @560 nm | % inhibition |
| Blank | 0.194 | | 0.250 | |
| 20 | 0.165 | 14.95 | 0.038 | 84.80 |
| 40 | 0.097 | 50.00 | 0.037 | 85.20 |
| 60 | 0.064 | 67.01 | 0.029 | 88.40 |
| 80 | 0.050 | 74.23 | 0.027 | 89.20 |
| 100 | 0.038 | 80.41 | 0.026 | 89.60 |

4.3. Reducing Power Assay

The reductive ability of the samples was determined by Oyaizu, 1986. The test samples were mixed with 2.5 ml of 0.2 M phosphate buffer (pH 6.6) and 2.5 ml of 1% potassium ferricyanide [$K_3Fe(CN)_6$]. Reaction mixture was incubated at 50° C. for 20 min, added 2.5 ml of 10% trichloroacetic acid, then centrifuged (650 rpm at room temperature) for 10 min. The upper layer solution (2.5 ml) was mixed with 2.5 ml of distilled water and 0.5 ml of 0.1% $FeCl_3$. Absorbance was measured at 700 nm. Higher absorbance at 700 nm indicates higher reducing power ability.

Results

Figure 9:
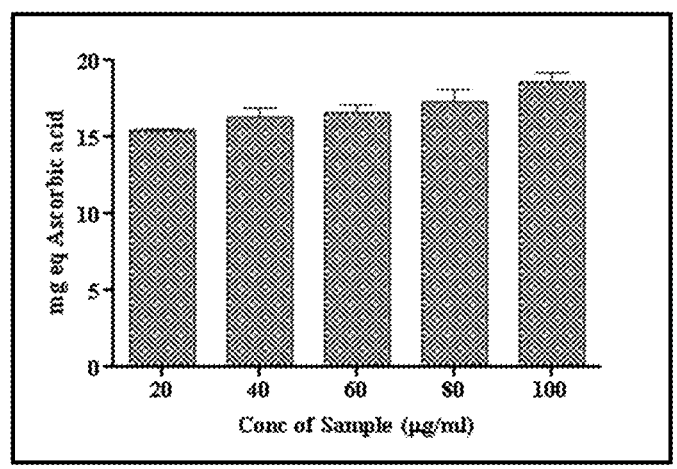
FIG. 9 shows total antioxidant capacity of an embodiment of the inventive composition.

As illustrated in FIG. 4, $Fe^{3+}$ to $Fe^{2+}$ transformation in the presence of the composition and reference compound ascorbic acid was performed to measure the reductive capability. Throughout the concentration range (20-100 μg/ml), the composition and the standard showed nearly the same trend in their reductive capability, although all the composition exhibited a lower activity than the standard. At a concentration of 100 μg/ml, absorbance of the composition and ascorbic acid was found to be 0.660 and 0.970 respectively (Table 7 and FIG. 9).

TABLE 7

Reducing Power Activity

| Conc. in μg/ml | Composition | Ascorbic acid |
|---|---|---|
| 20 | 0.087 | 15.46 |
| 40 | 0.098 | 16.60 |
| 60 | 0.102 | 16.61 |
| 80 | 0.111 | 17.33 |
| 100 | 0.127 | 18.59 |

4.4. Total Antioxidant Activity

The phosphomolybdenum method is based on the reduction of Mo (VI) to Mo (V) by the antioxidant compound and the formation of a green phosphate/Mo (V) complex with a maximal absorption at 695 nm. The antioxidant activity of the test sample was determined by the phosphomolybdenum method as described by Prieto et al. 1999. Briefly, 0.3 ml of test sample combined with 3 ml of reagent solution (0.6 M sulfuric acid, 28 mM sodium phosphate and 4 mM ammonium molybdate). The reaction mixture was incubated at 95° C. for 90 min and cooled to room temperature. Measured the absorbance of the solution at 695 nm against blank. The total antioxidant capacity is expressed as the number of equivalents of ascorbic acid (AAE).

Results

Figure 10:
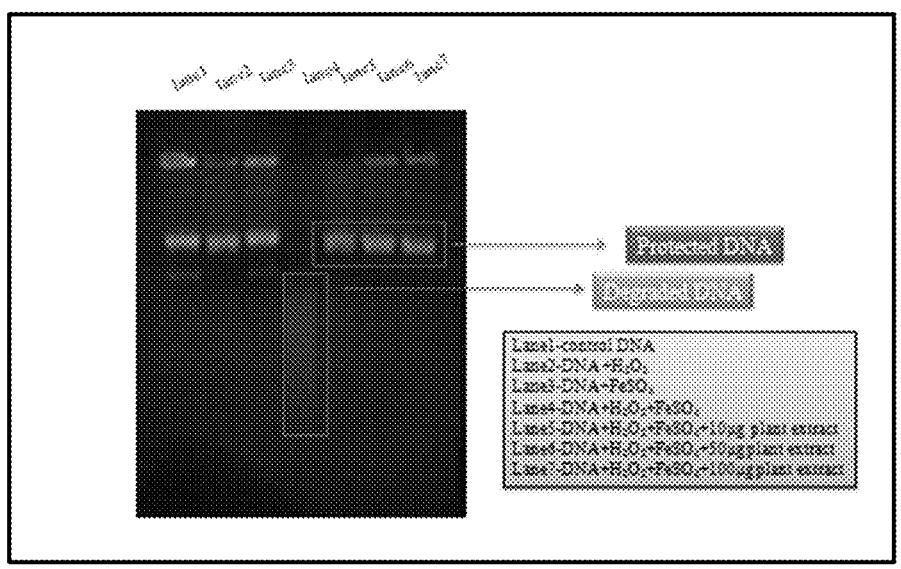
FIG. 10 shows the protective role of an embodiment of the inventive composition against oxidative DNA damage.

Total antioxidant capacity of the composition, expressed as the number of gram equivalents ascorbic acid, is shown in Table 8. FIG. 10 shows the reductive capabilities of the composition and it was found remarkable. The reducing power of the composition was observed to rise in a dose-dependent manner.

TABLE 8

Determination of Total Antioxidant Activity Protective Effect on DNA Scission-Induced by Hydroxyl Radical

| Conc. in µg/ml | Composition | |
|---|---|---|
| | Absorbance @695 nm | AAE |
| 20 | 0.087 | 15.46 |
| 40 | 0.098 | 16.60 |
| 60 | 0.102 | 16.61 |
| 80 | 0.111 | 17.33 |
| 100 | 0.127 | 18.59 |

Despite concerns regarding the specificity and validity of the TBA assay, viz. possible interference with hemoglobin or biliverdin present in the sample, potential thermal degradation due to heating during the assay, presence of iron in the assay reagents, rapid metabolism of MDA, and low representativeness of MDA among lipid peroxides (less than 1%), the assay is still chosen by several researchers and is thus useful for comparative purposes. Furthermore, OH. radicals can also enhance DNA damage, via attack on its phosphate bonds; this type of degradation results in smaller fragments, which can be separated by agarose electrophoresis.

In this assay hydroxyl radicals are typically generated within a mixture of ascorbic acid, $H_2O_2$ and $Fe^{3+}$-ethylenediaminetetracetic acid (EDTA); those radicals that are not scavenged by other components of the reaction mixture will eventually attack deoxyribose, thus degrading it into a series of fragments. Some of the fragments (or even all of them) react upon heating with thiobarbituric acid (TBA), at low pH, thus yielding a pink chromogen: this TBA adduct possesses a three-carbon dialdehyde, malondialdehyde (MDA). If an OH scavenger is meanwhile added to the reaction mixture, it will compete with deoxyribose for OH radicals, and consequently inhibit deoxyribose degradation. Reaction Mixture: (Xican Li et. al)

The experiment was conducted using calf thymus DNA. Briefly, the sample was dissolved in ethanol at 1 mg/mL. 50 µl of different concentration of sample was then separately taken into mini tubes followed by addition of 400 µL of phosphate buffer (0.2 mol/L, pH 7.4). Subsequently, 50 µL DNA sodium, 50 µL $H_2O_2$, 50 µL $FeCl_3$ and 50 µL $Na_2EDTA$ (1 mmol/L) were added. The reaction was initiated by adding 50 µL ascorbic acid (18 mmol/L) and the total volume of the reaction mixture was adjusted to 800 µL with buffer. After incubation in a water bath at 55° C. for 20 min, the reaction was terminated by adding 250 µL TCA.

Figure 11:
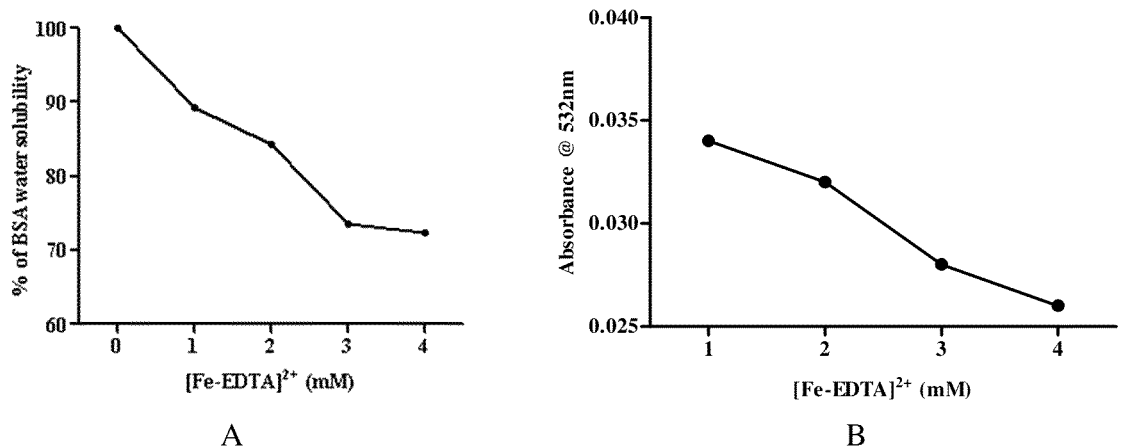
FIG. 11 shows, for an embodiment of the inventive composition, (A) insolubilization of BSA exposed to Fenton's reaction system, and (B) determination of OH⁻ radical at different concentrations of chelated iron (Fenton's reaction system).

The color was then developed by addition of 150 µL of TBA and heating in an oven at 105° C. for 15 min. The mixture was cooled and absorbance was measured at 532 nm against the buffer (as blank). The percent of protection against DNA damage is expressed Protective effect %=$(1-A/A_0)\times100$ Where $A_0$ is the absorbance of the mixture without sample, and A is the absorbance of the mixture with sample.
Results It is well known that hydroxyl radical (OH) is generated in human body via Fenton reaction. Since OH radical has extreme reactivity, it can easily damage DNA to produce malondialdehyde (MA) and various oxidative lesions. MDA combines TBA (2-thiobarbituric acid) to produce TBARS (thiobarbituric acid reactive substances) which resent a maximum absorbance at 530 nm. On the other hand, as the oxidative lesions have no conjugative system in the molecules, they cannot be detected by a spectrophotometer at 530 nm. It means that these oxidative lesions can bring about no interference with the determination of MDA. Hence, the value of $A_{532}$ can evaluate the amount of MDA, and ultimately reflect the extent of DNA damage Based on the formula "protective effect", it can be deduced that the decrease of $A_{532}$ value indicates a protective effect against DNA damage. As seen in above graph when compared to Standard BHA, the composition dose dependently increased the protective effect against DNA damage from 10-100 µg/mL. At 100 µg concentration the percentage protective effect of the composition and BHA was found to be 91.82% and 51.37% respectively (Table 9 and FIG. 11).

TABLE 9

DNA protectivity by using BHA as a Standard

| Concentration in | % protective effect | |
|---|---|---|
| µg/ml | BHA | Composition |
| 10 | 15.79 ± 0.89 | 87.03 ± 0.19 |
| 20 | 19.25 ± 1.09 | 87.80 ± 0.63 |
| 40 | 32.50 ± 2.12 | 89.03 ± 1.41 |
| 60 | 39.16 ± 0.33 | 90.54 ± 0.79 |
| 80 | 43.04 ± 0.29 | 91.41 ± 0.74 |
| 100 | 51.37 ± 4.06 | 91.82 ± 0.41 |

4.5. Protective Role Against Oxidative DNA Damage

This assay was based on the ability of the composition of Example 1 to protect the plasmid DNA pBR322 against damage caused by hydroxyl (OH) radicals. Hydroxyl radicals generated by the Fenton reaction are known to cause oxidatively induced breaks in DNA strands, resulting in decreased super coiled form and conversion to its open circular forms. Exposure of plasmid DNA to Fenton's reagent ultimately results in strand breaks, mainly due to the generation of reactive species-hydroxyl radical and the subsequent free radical-induced reaction on plasmid DNA. Hydroxyl radicals react with nitrogenous bases of DNA producing base radicals and sugar radicals. The base radicals in turn react with the sugar moiety causing breakage of sugar phosphate backbone of nucleic acid, resulting in strand break.

Figure 12:
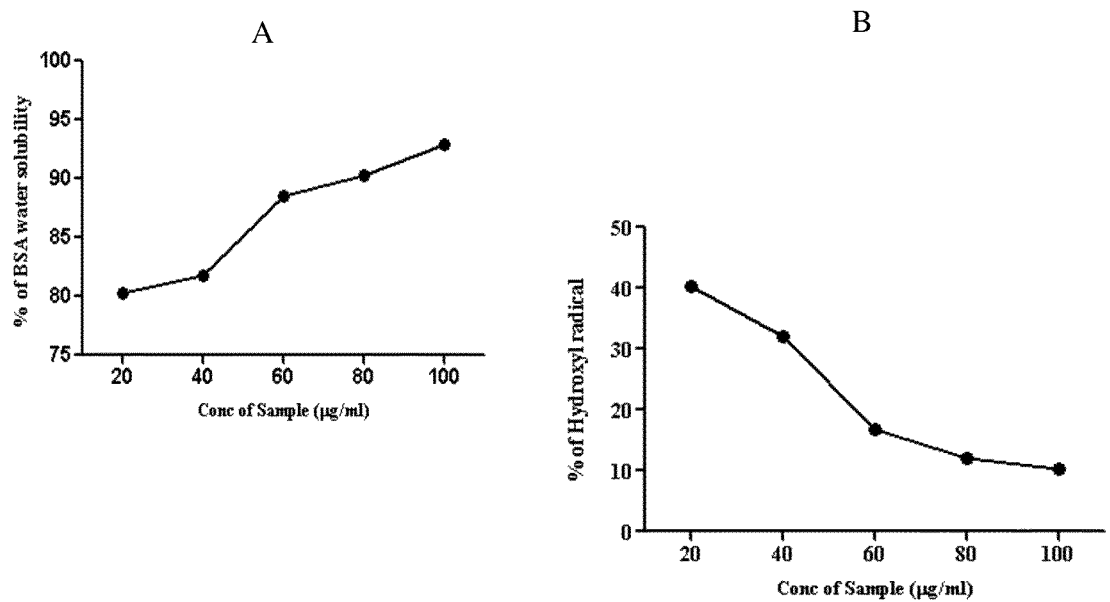
FIG. 12 shows the effect of an embodiment of the composition on (A) the solubility of BSA exposed to Fenton's reaction system (3 mM chelated iron concentration), and (B) hydroxyl radical scavenging.

Plasmid DNA (pBR322) with a concentration of 0.5 µg/3 µl was treated with Fenton's reagent (30% $H_2O_2$+2 mM $FeSO_4$) and different concentrations of composition (10 µg, 50 µg and 100 µg) incubated for 1 hour at 37° C. At the same control DNA, DNA treated with 2 mM $FeSO_4$, DNA treated with 30% $H_2O_2$, DNA treated with 2 mM $FeSO_4$ and 30% $H_2O_2$) were run simultaneously. Each mixture was incubated at 37° C. for one hour. After incubation, 3 µl (6× loading dye) was added to each reaction mixture, the samples were loaded on a 1% agarose gel and visualized with UV illuminator.
Results The DNA damage study is a reliable assay to evaluate the protective role of an agent against ROS mediated oxidative stress. Protection of vital biological macromolecules such as nucleic acids is the major mechanism by which the drugs do exert their antioxidant property. In the present study, the composition showed DNA protection against damage induced by Fenton's reagent. The composition at concentrations of 50 and 100 μg was highly effective in retaining the structural integrity of plasmid DNA as evident in FIG. 12.

4.6 Protective Role Against the Hydroxyl Radical Mediated Cross-Linking of Proteins In Vitro In the last decades there has been an increasing interest in the role that reactive oxygen species (ROS) and antioxidants may play in the ageing process and in the development of diseases associated with old age. Increased amount of oxidized proteins have been experimentally demonstrated in the ageing human brain and many rodent tissues (Floyd et al., 2001). There is evidence for the increase in the rate of ROS production and subsequent rate of ROS mediated protein damage with age. The involvement of oxidative damage in aging has prompted studies to examine the expected beneficial effects of antioxidant supplementation.

It was considered worthwhile to study the antioxidant properties of the composition in a non-lipid environment of a pure protein. Hence, the method of Zs.-Nagy and Nagy, 1980 for recording changes in water solubility of the model protein bovine serum albumin (BSA) exposed to free radicals generated by an inorganic chemical system was adopted. In the present study, the Fenton reaction system of $Fe^{2+}/EDTA/H_2O_2$ as a source of free radicals was used to prove the composition to protect BSA against free radical mediated cross-linking.

Protein Cross-Linking

Bovine serum albumin (BSA), a completely water-soluble protein, was polymerized by hydroxyl radicals generated by the Fenton reaction system of $Fe^{2+}/EDTA/H_2O_2$. As a result, the protein loses its water solubility and the polymerized product precipitates. The decrease in the concentration of the water soluble protein can be easily detected.

The in vitro incubation mixtures contained reagents, added in the sequence as follows, at the final concentrations: BSA (0.8 mg/ml), phosphate buffer, pH 7.4 (10 mM), water to reach 2.5 ml total volume, various concentrations of the composition, EDTA (0-4.8 mM), $FeSO_4$ (0-4 mM) and $H_2O_2$ (0.2%). To chelate iron completely 1.2 molar excess of EDTA was always used. The reaction mixture was incubated for 20 min at ambient temperature then centrifuged at 3500 rpm for 10 min. The supernatant was precipitated with an equal volume of trichloroacetic acid (10%) at 0° C. followed by centrifugation at 3500 rpm for 10 min. The precipitate thus obtained was redissolved in 1 ml of $Na_2CO_3$ (10%) in NaOH (0.5 M) and the final volume made up to 2.5 ml by water. An aliquot of the solution was used for protein determination using Bradford reagent (Sigma). The yield of OH radicals generated in the incubations was determined on the basis of degradation of deoxyribose as described by Halliwell et al., 1987.

SDS-PAGE Electrophoresis

The 0.5 mg protein pellets isolated from the incubation mixtures of BSA with the Fenton system as described above, in the presence of 4 mM ferrous sulfate, were treated with 5% SDS either in the presence or absence of 5% 2-mercaptoethanol. Electrophoresis was conducted with stacking and separating gels containing 4 and 7.5% acrylamide, respectively. The gels were stained in 0.2% coomassie blue, and destained in 10% acetic acid in 25% methanol.

Results

Figure 13:
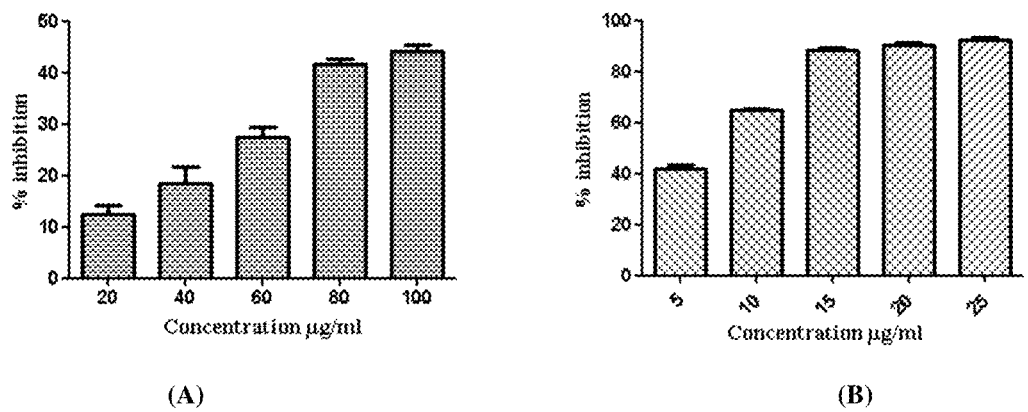
FIG. 13 shows comparative inhibition of pancreatic lipase activity by (A) an embodiment of the inventive composition, and (B) Orlistat.

The present work recorded the changes in water solubility of BSA exposed to chemical source of hydroxyl free radicals to characterize the anti-oxidant efficiency of the composition of Example 1 in a non-lipid protein system. The Fenton reaction system which gave a defined flow of hydroxyl radicals was used. Deoxyribose was used as a detection molecule to determine the yield of hydroxyl radicals in the Fenton's reaction system. BSA, a completely water-soluble protein, exposed to the above Fenton's reaction system, was losing its water solubility depending on the concentration of the chelated iron, as shown in FIG. 13A. The initial insolubilization was noticed at 1 mM iron and slow up to 2 mM followed by an exponential decrease in % solubility of BSA at higher concentrations. The OH. radical decreased with increased concentration of chelated iron (1-4 mM) as the radicals were used up to polymerize BSA (FIG. 13B).

Figure 14:
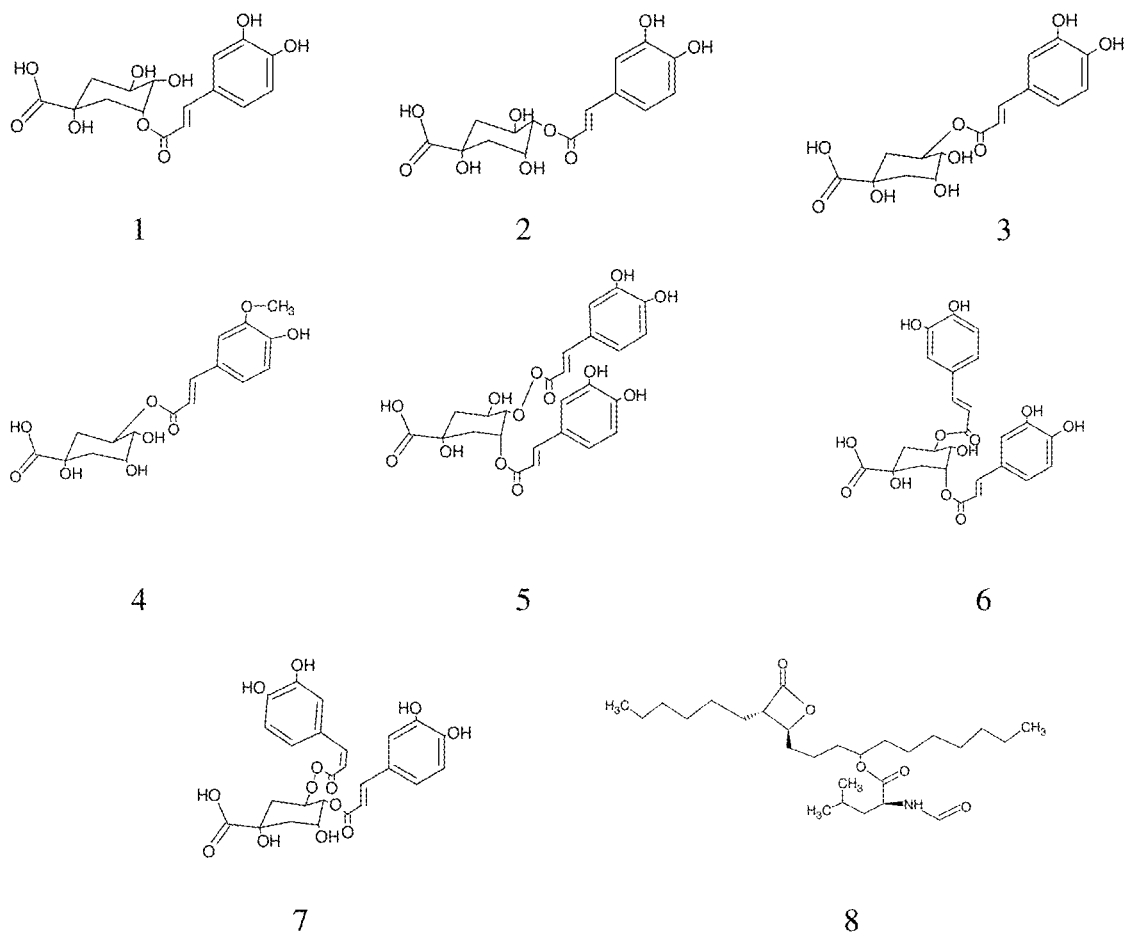
FIG. 14 shows the structure of ligand molecules (1) 3-O-Caffeoylquinic acid, (2) 4-O-Caffeoylquinic acid, (3) 5-O-Caffeoylquinic acid, (4) 5-O-Feruloylquinic acid, (5) 3,4-O-Dicaffeoylquinic acid, (6) 3,5-O-Dicaffeoylquinic acid, (7) 4,5-O-Dicaffeoylquinic acid, and (8) Orlistat.

The composition was added to the BSA incubations and inhibited protein cross-linking in a concentration-dependent way as shown in FIG. 14A. Similarly, the composition of Example 1 was effective in scavenging the OH. radicals generated by the Fenton's reaction system (FIG. 14B). There was a significant correlation observed between the BSA solubility and the OH. radicals indicating a critical role of free radicals in BSA cross-linking under the conditions employed in this study.

The results obtained in this study strongly indicated that the insolubilization of BSA induced by the Fenton's system of $Fe^{2+}/EDTA/H_2O_2$ was caused by free OH. radical mediated polymerization giving rise to true covalent cross-links. The model system was found suitable for convenient testing of OH. radical scavenging and hence the protective role of the composition in a non-lipid environment.

Example 5—Effect of Composition in Obesity Management 5.1 In Vitro Anti-Lipase Activity In order to provide the scientific evidence for the effectiveness of the composition of Example 1 in managing obesity, the in vitro anti-lipase assay using the porcine pancreatic lipase activity was used as a measure. Substrate: 10 mM p-NPB (p-nitrophenylbutyrate)

Enzyme: Porcine Pancreatic Lipase

The ability of the composition to inhibit pancreatic lipase was measured using the method previously reported by Kim et al., 2012. Briefly, an enzyme buffer was prepared by the addition of 6 μL porcine pancreatic lipase solution (Sigma-Aldrich) in buffer containing 10 mM MOPS (morpholinepropanesulphonic acid) and 1 mM EDTA, pH 6.8, to 169 μL Tris buffer (100 mM Tris-HCl and 5 mM $CaCl_2$, pH 7.0). Then, 20 μL of the composition at the test concentration (20-100 μg/mL) was mixed with 175 μL enzyme buffer and incubated for 15 min at 37° C. with 5 μL substrate solution (10 mM p-NPB (p-nitrophenylbutyrate) in dimethyl formamide); the enzymatic reactions were allowed to proceed for 15 min at 37° C. Lipase activity was determined by measuring the hydrolysis of p-NPB top-nitro phenol at 405 nm using UV spectrophotometer. Inhibition of lipase activity was expressed as the percentage decrease in OD when porcine pancreatic lipase was incubated with the test materials. Lipase inhibition (%) was calculated according the following Formula:

$$\text{Inhibition \%}=100-\{B-b/A-a\times100\}$$

where 'A' is the activity without inhibitor, 'a' is the negative control without inhibitor, 'B' is the activity with inhibitor, and 'b' is the negative control with inhibitor.

Figure 15:
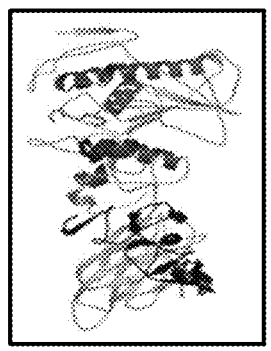
FIG. 15 shows the 3D structure of pancreatic lipase.

The results were expressed as an average. Inhibition of pancreatic lipase is expressed in terms of percentage. The composition exhibited an inhibitory effect on lipase with a maximum percentage inhibition of 44.08% at a concentration of 100 μg/mL. The results though were comparable to standard drug Orlistat, the composition was not more effective than the positive control (FIG. 15). However, Orlistat has been associated with side effects such as gas with oily spotting, stomach pain, irregular menstrual periods, and headaches.

Results

The results of anti-lipase activity were expressed as the percentage inhibition of pancreatic lipase and the composition had shown appreciable inhibitory spectrum at various concentrations tested. There was a moderate decrease in the enzyme activity as evident by the gradual increase in percentage inhibition following incubation with the composition. The results were comparable to standard drug Orlistat (FIG. 15).

5.2 in Silico Docking Studies with Human Pancreatic Lipase

Figure 16:
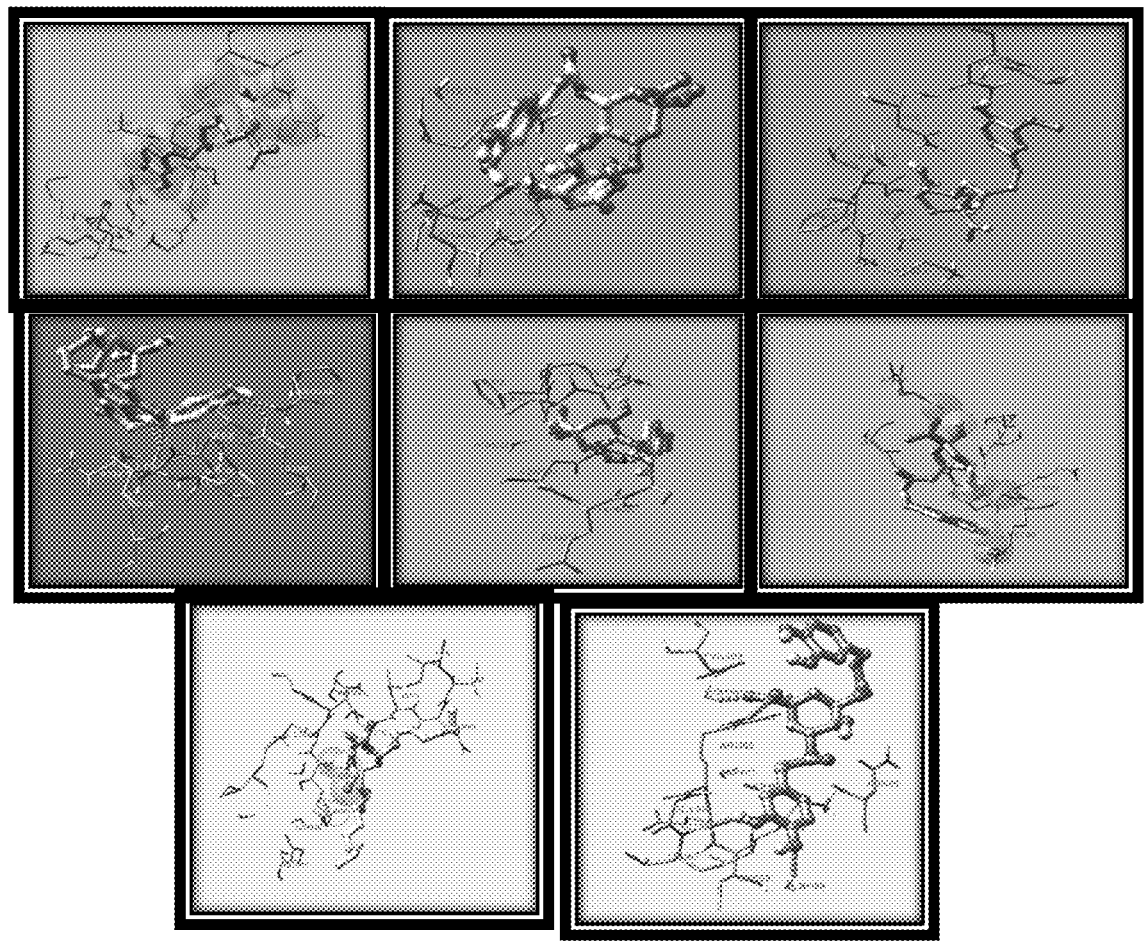
FIG. 16 shows the orientation of ligands in the active pocket of pancreatic lipase for (A) 3-O-Caffeoylquinic acid, (B) 4-O-Caffeoylquinic acid, (C) 5-O-Caffeoylquinic acid, (D) 5-O-Feruloylquinic acid, (E) 3,4-O-Dicaffeoylquinic acid, (F) 3,5-O-Dicaffeoylquinic acid, (G) 4,5-O-Dicaffeoylquinic acid, and (H) Orlistat.

In the present study, in order to evaluate the comparative inhibition of pancreatic lipase by the standard drug Orlistat and the composition, in silico docking analysis was performed. AutoDock tools was utilized to generate grids, calculate dock score and evaluate the conformers of inhibitors bound in the active site of pancreatic lipase as targets for anti-obesity activity. Automated docking is a graphical user interface. AutoDock 4.2 was employed to get docking and binding scores; which is implemented by Lamarckian genetic algorithm method. The ligand molecules i.e., the isomers of chlorogenic acid (FIG. 16) and Orlistat were designed and the structure was analyzed using ACD/Chemsketch. The PRODRG server was used to minimize energy of drug compounds and 3D coordinates were prepared. The protein structure file (PDB ID: 1LPB) (FIG. 17) was taken from PDB and was edited by removing the hetero atoms using Python molecule viewer. The grid map was centered at particular residues of the protein and was generated with AutoGrid. As per genetic algorithm all the torsions were allowed to rotate during docking. The Lamarckian genetic algorithm and the pseudo-Solis and Wets methods were applied for minimization, using default parameters (Rodriguez and Infante, 2011).

Results

Figure 18:
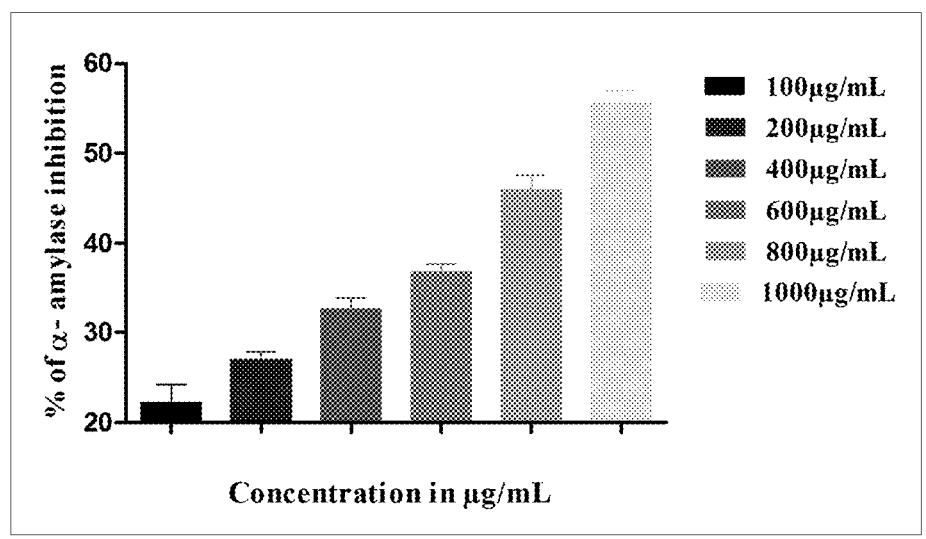
FIG. 18 shows the α-amylase activity inhibition by an embodiment of the inventive composition.

The isomers of chlorogenic acid in the composition exhibited pronounced lipase inhibition activity as evident from the thermodynamic parameters studied (Table 10). The interaction of isomers with active pocket residues was firm as it required lesser energy as compared to the standard drug Orlistat (FIG. 18). The study supports the claim for the anti-obesity effects of the composition as evident from the strong inhibition of pancreatic lipase by the isomers of chlorogenic acid.

The increased levels of systemic oxidative stress that occur in obesity may contribute to the obesity-associated development of secondary complications. Medicinal herbs have drawn attention during recent past in the obesity management mediated through various mechanisms including oxidative stress. Plants are a rich source of polyphenols, major group of biologically active secondary metabolites. These factors attribute mainly to the therapeutic benefits of plants including antioxidant activity. This scientific report is based on a comprehensive study in vitro and in silico analysis to validate the health benefits of the composition of Example 1 in obesity management.

Studies have suggested that excessive intake of calories are related to chronic diseases which includes obesity. These are all linked to oxidative stress, causing an imbalance of pro oxidants and antioxidants in cellular systems, which impairs normal biological functions (Droge, 2002).

Example 6—α-Glucosidase Inhibition

The inhibition of α-glucosidase activity of the extract from Example 1 was determined by adopting the standard method with slight modification. In a 96-well plate, reaction mixture containing 50 μl phosphate buffer (100 mM, pH=6.8), 10 μl α-glucosidase (1 U/ml), and 20 μl of varying concentrations the extract (0.1-1 mg/ml) were pre-incubated at 37° C. for 15 min. Then, 20 μl p-NPG (5 mM) was added as a substrate and incubated further at 37° C. for 20 min. The reaction was terminated by adding 50 μl $Na_2CO_3$ (0.1 M). The absorbance of the released p-nitrophenol was measured at 405 nm using multiplate reader. Without test substance was set up in parallel as a control and each experiment was performed in triplicates. The results were expressed as percentage inhibition.

$$AG = \frac{(A_{control} - A_{sample})}{A_{control}} \times 100$$

Where $A_{control}$ is the absorbance of the control mixture and $A_{sample}$ represents absorbance of samples containing the extracts. Applying convenient concentration of the test sample necessary to inhibit 50% activity of the enzyme (IC50) was calculated using regression analysis.

Example 7—α-Amylase Inhibition

The assay was carried out by adopting the standard protocol with slight modifications. Starch azure (2 mg) was suspended in 0.2 mL of 0.5M Tris-HCl buffer (pH 6.9)

TABLE 10

Molecular Docking Results of Pancreatic Lipase

| Molecule | Binding energy (kJmol$^{-1}$) | Ligand efficiency (kJ/mol$^{-1}$) | Inhibitory constant | H-bonds | Interactions |
| --- | --- | --- | --- | --- | --- |
| 3-O-Caffeoylquinic acid | −4.64 | −0.19 | 399.38 | 4 | Lys238, Asn10 |
| 4-O-Caffeoylquinic acid | −3.69 | −0.15 | 1.96 | 5 | Glu385, Ile371 Lys373, Glu370 |
| 5-O-Caffeoylquinic acid | −3.22 | −0.13 | 4.37 | 5 | Ile9, Lys39 |
| 5-O-Feruloylquinic acid | −3.39 | −0.13 | 3.25 | 4 | Ile371, Lys373 |
| 3,4-O-Dicaffeoylquinic acid | −1.3 | −0.04 | 111.7 | 6 | Asn406, Lys373 His354, Asn406 |
| 3,5-O-Dicaffeoylquinic acid | −2.58 | −0.07 | 12.9 | 4 | Glu15, Ile9 Asn240 |
| 4,5-O-Dicaffeoylquinic acid | −2.06 | −0.06 | 31.13 | 4 | Arg65, Glu64 |
| Orlistat (Std.) | −1.03 | −0.03 | 176.96 | 2 | Lys238 | containing 0.01 M $CaCl_2$) (substrate solution). The extract was dissolved in water in order to obtain concentrations of 100 μg-1000 μg. Then, 0.2 mL of the extract of different concentrations was added to the tube containing the substrate solution. In addition, 0.1 mL of porcine pancreatic amylase in Tris-HCl buffer (2 units/mL) was added to the tube containing the extract and substrate solution. The reaction was carried out at 37° C. for 10 min. The reaction was terminated by adding 0.5 mL of 50% acetic acid in each tube. The reaction mixture was centrifuged at 3000 rpm for 5 min at 4° C. The absorbance of resulting supernatant was measured at 595 nm using spectrophotometer (Shimadzu UV-VIS spectrophotometer). The α-amylase inhibitory activity was calculated by using s the equation for α-glucosidase assay.

Example 8—MTT Assay

Briefly, the cells ($5 \times 10^3$ per 96 well) were incubated at 37° C. in 5% $CO_2$ and 95% air with different concentrations of the extract. After 24 h, a 20 μL aliquot of 3-(4,5-Dimethylthiazol-2-yl)-2,5-diphenyltetraolium bromide (MTT, a yellow tetrazole; 5 mg/ml in PBS) was added to the wells and incubated further for 4 h at 37° C. The supernatant was removed carefully, 100 μl of DMSO was added and mixed, and the absorbance was read at 563 nm to determine the formazan concentration which is proportional to the number of live cells.

Example 9—Cell Culture and Adipocyte Differentiation

3T3-L1 mouse adipocytes were cultured in DMEM containing 10% FBS until confluent, and were then maintained in the same medium for an additional 2 days. Differentiation was induced 2 days post-confluence (day 0 of differentiation) by adding 0.5 mM IBMX, 1 mM dexamethasone, and 5 mg/mL insulin in DMEM with 10% FBS (MDI). After 2 days of incubation, culture medium was changed to fresh DMEM containing 10% FBS and 5 mg/mL insulin. Two days later, the medium was replaced with DMEM supplemented with 10% FBS and incubated for another two days. The extract was added two days after confluence (day 4) and maintained another two days (6 days) at which time more than 90% of the cells were mature adipocytes with accumulated fat droplets.

Intracellular lipid accumulation was measured using Oil Red O. The Oil Red O working solution was prepared as described by Ramirez-Zacarias et al. (16) The 3T3-L1 cells were fixed with 10% formalin and then stained for 1 h with a filtered solution of 60% Oil Red O in 100% aqueous 2-isopropanol. To quantify the intracellular lipids, the stained lipid droplets were dissolved in isopropanol (3 ml per well). The extracted dye was transferred into a 96-well plate and the absorbance was read with a Multiscan Ex microplate reader (Thermofischer) at 500 nm.

After 8-day differentiation in the presence of the extract, 3T3-L1 adipocytes were collected and lysed in ice-cold RIPA lysis buffer for 30 minutes. Protein concentrations were determined using a Bradford reagent. Equal amount of protein for each sample was loaded and separated on a 10% SDS-PAGE. After electrophoretic separation, the proteins were transferred to a nitrocellulose membrane using a semi-dry transfer and blocked with 5% skim milk for 1 hour at room temperature, and incubated with primary antibodies at 4° C. overnight. The nitrocellulose filters were then incubated with horseradishperoxidase conjugated secondary antibody at room temperature for 3 hours. Immunoreactive proteins were detected using the chemiluminescent ECL assay and quantified using the Molecular Imager software (Bio-Rad). C/EBPb expression was determined 2 days after the induction of cell differentiation in the presence or absence of the indicated concentrations of UA. The expression of each protein was present as fold of the loading control, b-actin.

Example 10—Results 10.1—α-Glycosidase and α-Amylase Activity

Figure 17:
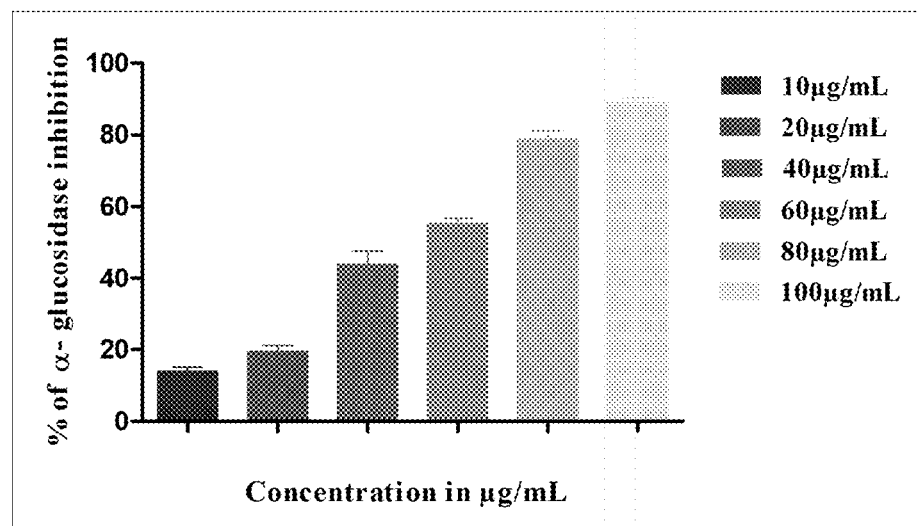
FIG. 17 shows the α-glucosidase activity inhibition by an embodiment of the inventive composition.

In order to determine the anti-diabetic potential of the extract, α-glycosidase and α-amylase activity inhibition assay were performed. It was noticed that the extract demonstrated dose dependent α-glucosidase inhibition activity, interestingly the extract at the concentration of 0.1 mg/mL showed 89.10% α-glucosidase activity inhibition (FIG. 17). Similarly, the α-amylase inhibitory activity was also assessed (FIG. 18). The inhibition of α-amylase by the extract (100-1000 μg/mL) showed concentration dependent α-amylase inhibitor activity. At the concentration of 1000 μg/mL, the extract showed 55.14% of α-amylase inhibition.

10.2—MTT Assay

Figure 19:
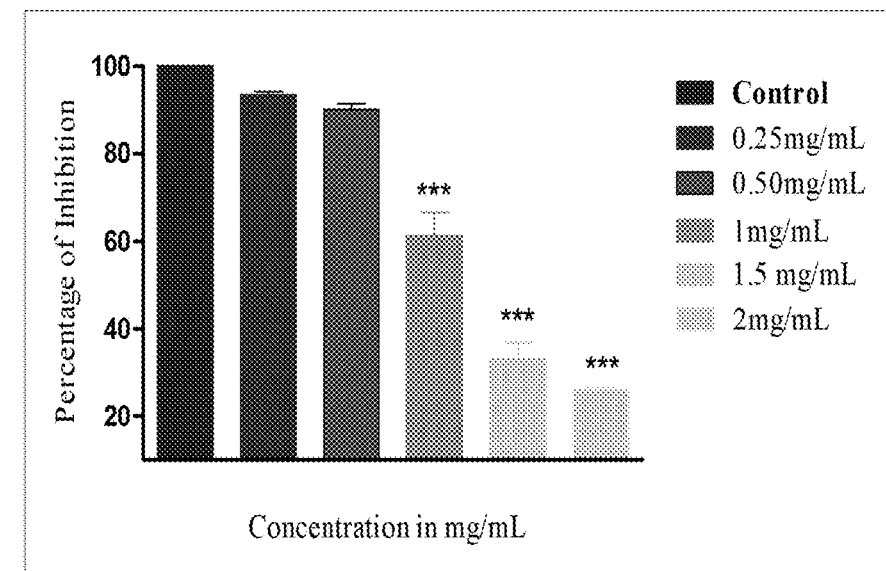
FIG. 19 shows the effect of an embodiment of the composition on cell viability in 3T3-L1 adipocytes.

Effect of the extract on 3T3L adipocyte cell viability was measured by MTT assay and the assay revealed that the extract at concentrations of 0.25-0.5 mg/mL did not affect cell viability (FIG. 19). Therefore, the concentration range of 0.25 and 0.5 mg/mL was chosen for further experiments.

10.3—Lipid Accumulation

Figure 20:
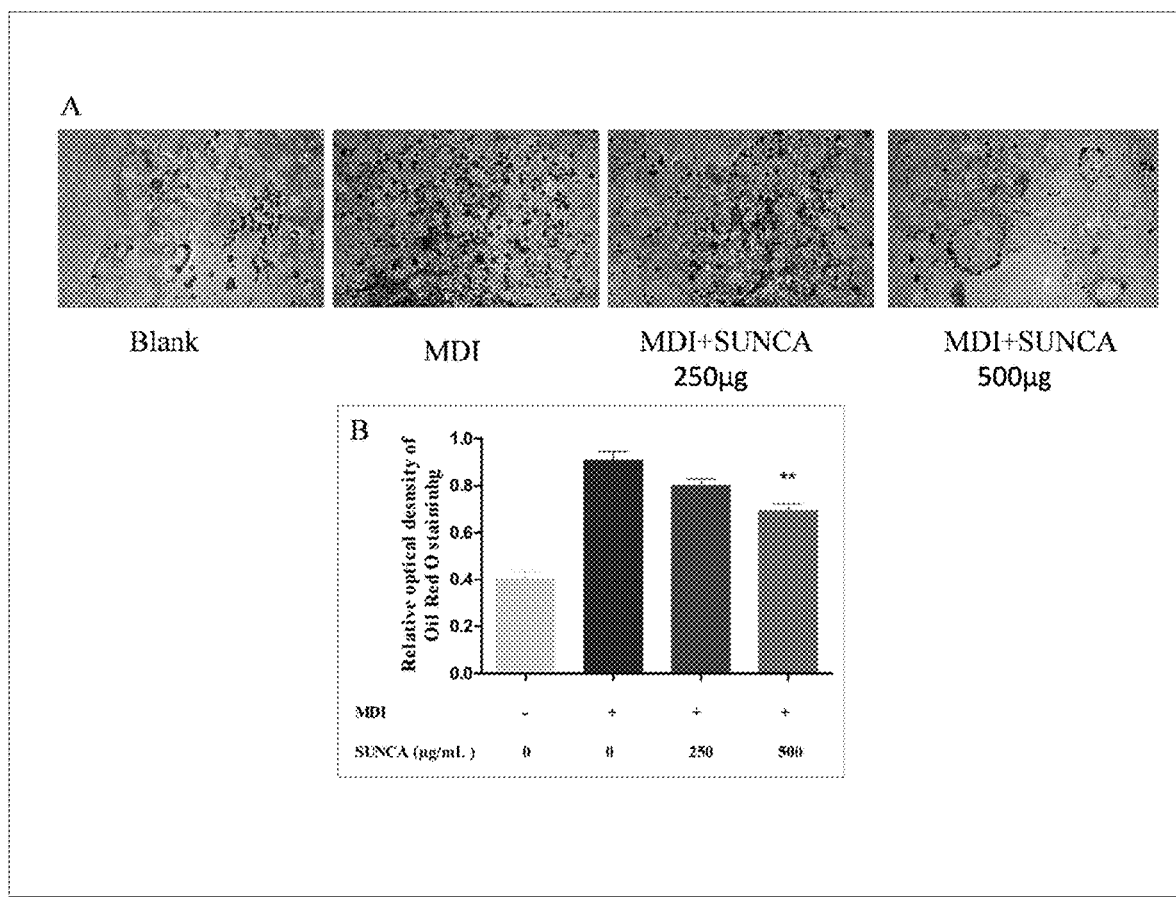
FIG. 20 shows the effect of an embodiment of the composition on lipid accumulation in 3T3-L1 cells. (A) Lipid droplets were measured by Oil Red O staining. (B) Lipid content was quantified by measuring absorbance.

In order to investigate the effects of the extract on preadipocyte differentiation, the lipid accumulation was measured by an Oil Red O staining assay. The 3T3-L1 cells were treated with 250 and 500 μg/mL of the extract during differentiation. As shown in FIGS. 20A and 20B, the extract suppressed lipid accumulation in 3T3-L1 adipocytes at levels that were statistically significant ($p<0.05$), showing the extract can inhibit adipogenesis in 3T3-L1 cells.

10.4—PPARγ and C/EBPα Expression

Figure 21:
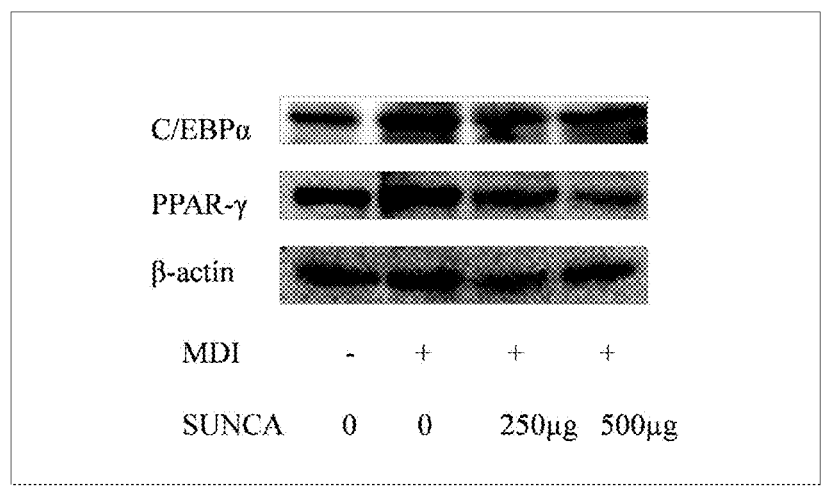
FIG. 21 shows the effect of an embodiment of the composition on the expression of PPARγ and C/EBPα during the differentiation in 3T3-L1 cells.

To investigate whether the extract suppresses adipogenesis through a PPARγ pathway, protein expression of PPARγ and C/EBPα were evaluated by Western blot analysis, after the treatment of fully differentiated cells with 250 and 500 μg/mL of the extract. The expressions of PPARγ and C/EBPα were dose dependently inhibited by the extract. PPARγ and C/EBPα protein levels were significantly reduced by treatment with 500 μg/mL of the extract (FIG. 21).

10.5—Expression Discussion

The treatment goal of diabetic patients is to maintain near normal levels of glycemic control, in both fasting and post-prandial conditions. Many natural sources have been investigated with respect to suppression of glucose production from the carbohydrates in the gut or glucose absorption from the intestine (Jo et al. 2011). Alpha-amylase catalyzes the hydrolysis of alpha-1,4-glycosidic linkages of starch, glycogen and various oligosaccharides. Alpha-glucosidase further breaks down the disaccharides to simple sugars, readily available for intestinal absorption. The inhibition of their activity in the digestive tract of humans is considered to be effective tool to control diabetes. In addition, these effects may lead to diminished absorption of monosaccharides (Kwon et al. 2006). Therefore, there is an urgent requirement of effective and nontoxic inhibitors of alpha-glucosidase and alpha-amylase. In the present study it was observed that the extract exhibited potent alpha-amylase and alpha glucosidase inhibitory activity. On the other hand, the effects of the extract on adipogenesis in mouse 3T3-L1 cells were examined. Oil Red O staining and lipid measurement results showed that the extract treatment robustly inhibited lipid droplet accumulation. Further characterization of the molecular mechanism of the anti-adipogenic effect indicated that the extract reduced the expression of the main adipogenic transcription factors, PPARγ and C/EBPα, at the translational levels. Based on these findings, it can be concluded that the extract showed effective in vitro anti diabetic and anti adipogenic activity.

Example 11—Anti-Obesity Effects In Vivo

The present study was designed to investigate the anti-obesity effects of the extract in high fat-diet (HFD) fed rats. Further the biomechanism of the extract mediated weight management was investigated in HFD rats.

11.1—Animals

Animal experiments were carried out taking appropriate measures to minimize pain or discomfort in accordance with the guidelines laid down by the NIH (USA) regarding the care and use of animals for experimental procedures and with due clearance from the Animals Ethical Committee (VHPL/PCL/IAEC/05/13) of CPCSEA. Forty male Sprague Dawley rats weighing between 180-200 g (Biogen Bangalore, India) were housed in clean poly propylene cages and maintained under 12 h light/12 h dark cycle. All the animals were fed with commercial pellet diet and water ad libitum for one week (acclimatization). The rats were divided into six groups (n=8): except control animals, all other groups were given high*-fat-diet (HD) with or without the extract (50, 100 and 150 mg/kg b.w.). The diets were given in the form of pellets for six weeks.

11.2—Experimental Design

Group I: Normal control (standard pellet diet)
Group II: Positive control (high fat diet)
Group III: High fat diet+the extract (50 mg/kg b.w.)
Group IV: High fat diet+the extract (100 mg/kg b.w.)
Group V: High fat diet+the extract (150 mg/kg b.w.)

TABLE 11

Composition of high fat-diet

| Ingredients | High fat diet (g/100 g diet) |
|---|---|
| Choline bitartrate | 0.2 |
| DL-methione | 0.3 |
| Vitamin mixture | 1 |
| Mineral mixture | 3.5 |
| Cellulose | 5 |
| Sucrose | 40 |
| Corn Starch | 10 |
| Casein | 20 |
| Bean oil | 5 |
| Lard | 15 |

Feed intake was recorded daily and the body weight of rats measured weekly once during the experiment. At the end of treatment, blood was drawn by retro orbital puncture; serum was separated by centrifugation at 1000×g for 15 minutes at 4° C. The animals sacrificed by overdose of anasthetics; visceral fat pads from different regions (epididymal, perirenal, mesenteric, and retroperitoneal regions) were excised, rinsed with phosphate-buffered saline (PBS), and stored at −80° C. until analysis.

Figure 22:
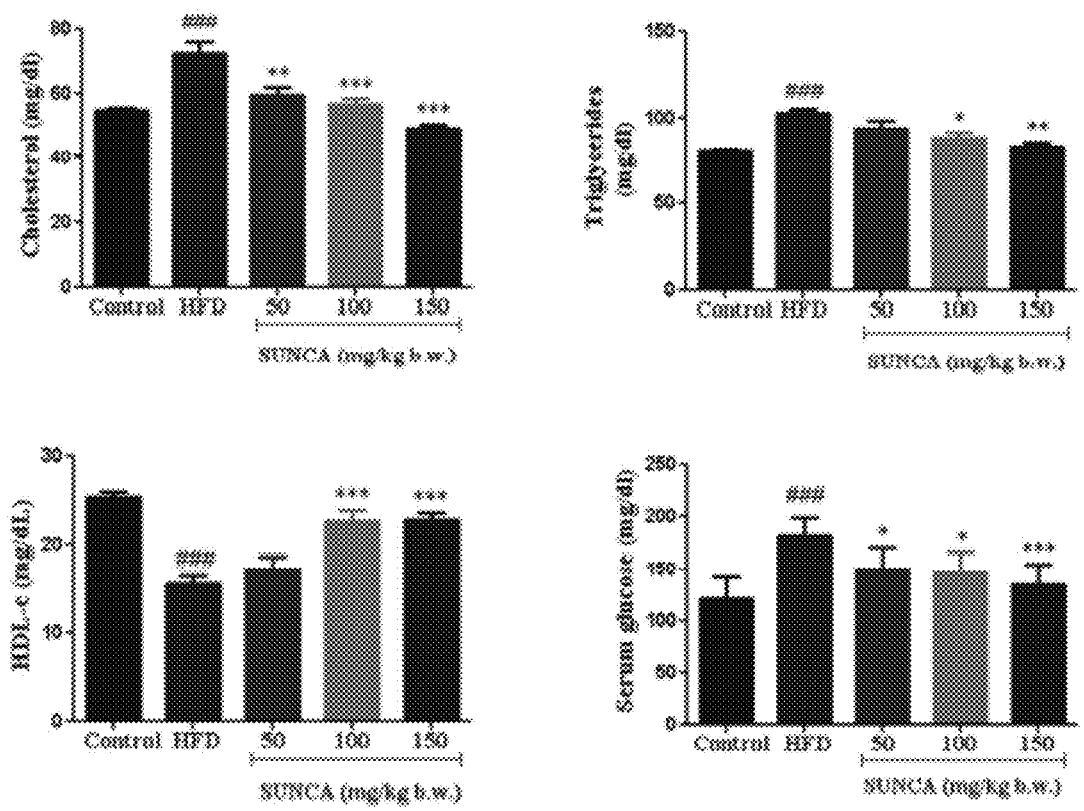
FIG. 22 shows the effect of an embodiment of the composition on serum concentrations of triglycerides, total cholesterol, glucose, and HDL.

The serum concentrations of triglycerides (TG), total cholesterol (TC), glucose, and HDL were measured enzymatically using commercial kits (ROBONIK Pretest kit and ACCUCARE™ kit from Lab-care Diagnostics Pvt Ltd.) (FIG. 22).

11.3—Preparation of Rat Liver Homogenates

Livers were rapidly excised, rinsed in ice-cold saline, and a 10% w/v homogenate was prepared using 0.15 M KCl, centrifuged at 800 g for 10 min at 4° C. The supernatant obtained was used for the ELISA and Western blotting.

11.4—Western Blot Analysis

Proteins from the liver tissues were extracted with a RIPA lysis buffer (50 mmol/L Tris, pH 7.4, 150 mmol/L NaCl, 1% Triton X-100, 1% sodium deoxycholate, 0.1% SDS, 1 mg/mL leupeptin, 50 mmol/L sodium fluoride, 1 mmol/L sodium orthovanadate, 1 mmol/L phenylmethylsulfonyl fluoride). Protein concentrations were determined by the Bradford method. Equal amounts of protein were separated by SDS-PAGE, and electro-transferred onto polyvinylidene difluoride (PVDF) membranes. The membranes were blocked with 3% BSA and TBS-T (50 mmol/L Tris HCl, pH 7.5, 150 mmol/L NaCl, 0.1% Tween 20) for 1 h at room temperature. The membranes were incubated overnight at 4° C. with primary antibodies in TBS-T. The membranes were washed three times with TBS-T (6 minutes each), and incubated with appropriate secondary antibodies for 1 h at room temperature. The blots were developed using X-ray films after applying the substrate.

11.5—Sandwich ELISA

Sandwich ELISA was performed with cell lysates using AMPK (pT172) ELISA kit from Life technologies. The total assay incubation time was only 4 hours. A monoclonal capture antibody specific for AMPKα has been coated onto the wells of the 96-well plate provided. During the first incubation, 100 µl of liver homogenates (1:100 dilution) were pipetted into the wells and the AMPKα antigen bound to the immobilized (capture) antibody. After washing, a rabbit antibody specific for AMPKα phosphorylated at threonine 172 was added to the wells. During the second incubation, this antibody served as a detection antibody by binding to the immobilized AMPKα protein captured during the first incubation. After washing, a horseradish peroxidase—labeled anti-rabbit IgG was added. This binds to the detection antibody to complete the four-member sandwich. After a third incubation and washing to remove the entire unbound enzyme, a substrate solution (Tetramethyl benzidine, TMB) was added, which was acted upon by the bound enzyme to produce color. The intensity of this colored product was directly proportional to the concentration of AMPKα [pT172] present in the original specimen, and the optical density read on a standard microplate reader.

11.6—Statistical Analysis

Data were expressed as mean±SEM and analyzed by one-way ANOVA followed by Dunnett's t test using Graph-Pad Prism version 5. Differences were considered statistically significant at $p<0.05$.

11.7—Results

Figure 23:
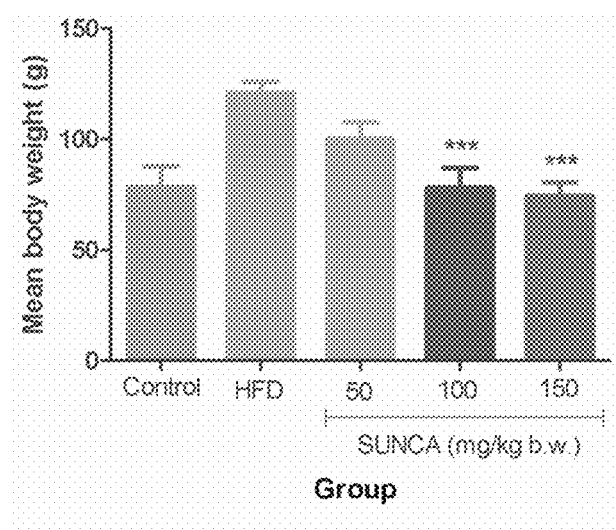
FIG. 23 shows the effect of an embodiment of the composition on mean body weight (n=8). Data were analyzed by one way ANOVA followed by Dunnett's test. ***p<0.001 compared to HFD group.
Figure 24:
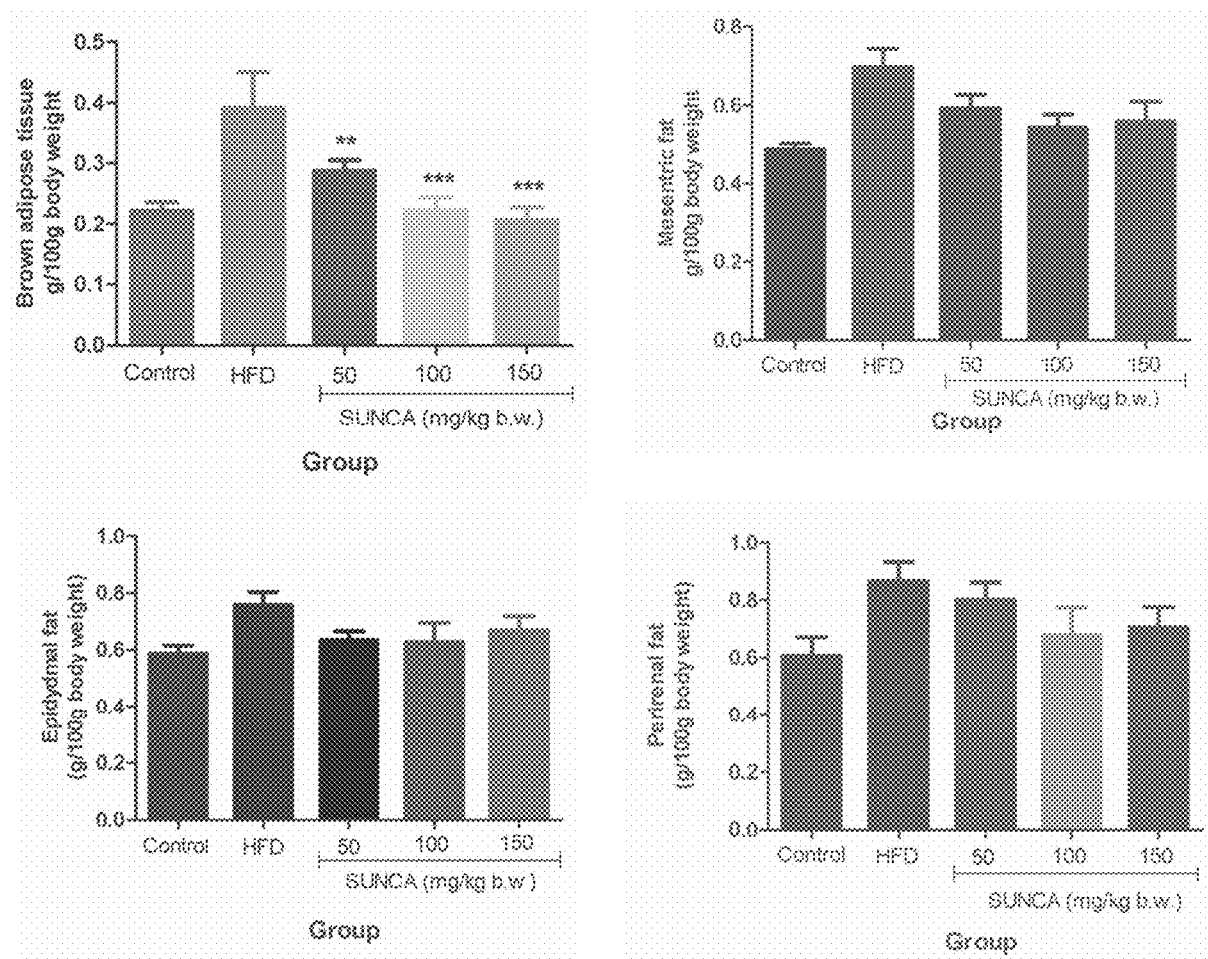
FIG. 24 shows the effect of an embodiment of the composition on fat weight (n=8). Data were analyzed by one way ANOVA followed by Dunnett's test. p<0.01, *p<0.001 compared to HFD group.

Administering the extract effectively alleviated the obesity conditions in HFD rats. There was a significant decrease in the mean body weight among the rats treated with different doses of the extract (FIG. 23). The data were highly significant in 100 and 150 mg/kg b.w. the extract treated animals ($p<0.001$). Further there was a significant dose-dependent decrease in the brown adipose tissue weight in the extract treated groups as compared to the HFD rats (FIG. 24). The data were significant at all the test doses of the extract. It was observed that mesenteric, epididymal and perirenal fat weights also decreased following the extract treatment when compared to HFD rats.

Figure 25:
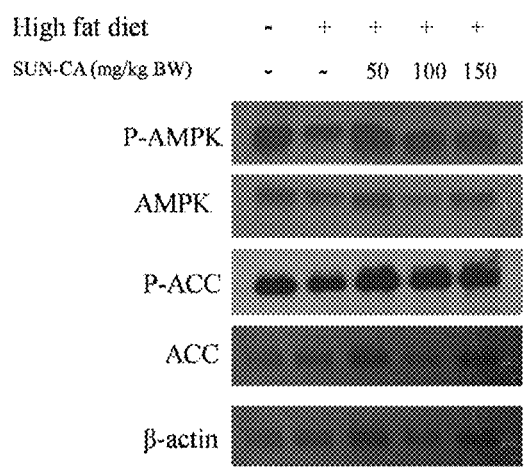
FIG. 25 shows the effect of an embodiment of the inventive composition on the protein expression of AMPK and ACC in liver of high fat diet rats.

The expression of proteins AMPK and ACC were determined by Western blot analysis. AMPK is a key mediator in the control of intracellular lipid metabolism, including the uptake, synthesis and oxidation of fatty acid in liver. The extract significantly activated hepatic AMPKα subunit by phosphorylating AMPKα at the Thr-172 residue in hyperlipidemic rats. Further, the activity of ACCα, downstream protein of AMPK was inhibited following extract treatment in rats. It was clearly shown that the hepatic expression of phosphorylated form of ACCα was unregulated in the extract-treated groups (FIG. 25).

Figure 26:
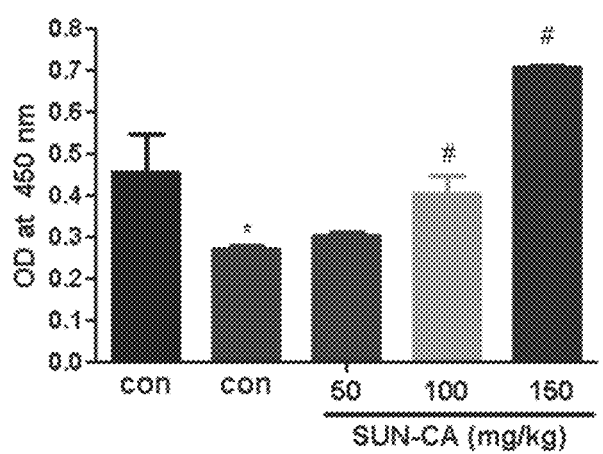
FIG. 26 shows the effect of an embodiment of the inventive composition on the activation of AMPK in rat liver. Data are mean±SEM values of three individual experiments. The values were compared with the control using analysis of variance followed by unpaired student's t tests. *p<0.05, significant differences from the normal control group. #p<0.05, significant differences from the positive control group.

Effect of the extract on the activation of AMPK in rat liver was further confirmed through ELISA. Administering the extract to obese rats significantly increased the AMPK levels compared to the high fat diet fed rats (FIG. 26). AMPK is one of the key regulatory enzymes involved in catabolism of free fatty acids (FFA) and inhibition of triglyceride (TG) accumulation. AMPK levels are low in obesity condition as evident in the experiment. However, the extract exerts its anti-obesity mechanism by elevating the activated form of AMPK assisting in the metabolism of FFA thereby decreasing FFA accumulation.

Example 12—Identification of PPAR α/PPAR γ Dual Agonists

Peroxisome proliferator-activated receptors (PPARs) play pivotal role in regulating the expression of proteins involved in glucose and lipid metabolism, adipogenesis and insulin sensitivity (Francis et al. 2003). PPARs are ligand inducible transcription factors that activate transcription in response to the binding of synthetic or natural ligands. To date, three subtypes of PPAR have been identified: PPARα, γ and δ; each differing in their physiological role and tissue distribution (Berger and Moller, 2002). PPARα positively regulates the fatty acid oxidation, and is involved in energy homeostasis (Harmon et al. 2011). PPARγ is predominantly expressed in adipose tissue where it regulates lipogenesis. PPARγ is also known to improve insulin sensitivity in skeletal muscle cells (Zieleniak et al. 2008). Agonists of PPARα and γ are effective in treating dyslipidemia and type 2 diabetes respectively (Shearer and Billin, 2007; Willson et al. 2000). PPARγ agonists such as Thiozolidinediones (TZDs) potentially target the adipose tissue and improve insulin sensitivity. TZDs (e.g., Pioglitazone, Rosiglitazone) are associated with side effects such as weight gain, congestive heart failure and edema (Kahn et al. 2008). Many novel agonists of PPARγ have been discovered so far, however, there is a growing interest in the search for PPARγ partial agonists that can exert higher antidiabetic effects with minimal side effects as compared to the full agonists.

Current research on the search for novel PPAR regulators is focused more on exploring the potential of selective PPARγ modulators (SPPARMS). SPPARMS exhibit improved glucose homeostasis with reduced side effects unlike the full agonists (Balakumar and Kathuria, 2012; Higgins and Depaoli, 2010). Further, discovery of compounds which can act as dual or pan agonists activating simultaneously two or all the three subtypes of PPAR receptors respectively can be therapeutically more beneficial (Heald and Cawthorne, 2011; Tenenbaum and Fisman, 2012).

Plant-based products are a rich source of bioactive compounds and provide large scope for the development of new drugs (Beutler 2009). Diverse chemical scaffold and drug likeliness makes the herbal products an excellent source for the discovery of potent drugs (Cragg and Newman, 2013). Significant efforts have been made to explore the potentials of natural products as PPAR agonists. Genistin, Kaempferol, quercetin, tocotrienols, commipheric acid, bixin and norbixin are to name a few PPARγ agonists (Takahashi et al. 2009; Cornick et al. 2009; Fang et al. 2010; Fang et al. 2008; Dang et al. 2003).

12.1—Method

Docking studies of CGA isomers with ligand binding domain (LBD) of PPARγ and PPARγ were performed using the Schrödinger software suite.

12.2—Preparation of Protein Target Structures

The crystal structures of the proteins PPARγ (PDB ID: 2ZNN) and PPARγ (PDB ID: 1ZGY) were retrieved from the RCSB protein data bank (PDB). The protein structures were pre-processed and refined using the following procedures by the Protein Preparation Wizard in the Schrödinger software suite, including adding hydrogen atoms, assigning partial charges and protonation states, and structure minimizing.

12.3—Ligand Preparation

The ligand structures were downloaded from Pubchem and saved in SDF file format. Subsequently they were prepared using LigPrep (Schrödinger) by modifying the torsions and assigning protonation states. In Glide (Schrödinger), 32 stereochemical structures were generated per ligand with possible states at target pH 7.0±0.5 using Ionizer, tautomerized, desalted and optimized by producing low energy 3D structure for the ligand under the OPLS 2005 force field while retaining the specified chiralities of the input Maestro file.

12.4—Receptor Grid Generation

Receptor grids were calculated for prepared proteins such that various ligand poses bind within the predicted active site during docking. In Glide, grids were generated keeping the default parameters of van der Waals scaling factor 0.8 and charge cutoff 0.25 subjected to OPLS 2005 force field. A cubic box of specific dimensions centered around the centroid of the active site residues (predicted by Sitemap) was generated for each receptor.

12.5—Ligand Docking

Extra precision ligand docking was performed in Glide of Schrödinger-Maestro v11.2. Van der Waals scaling factor and partial charge cutoff was selected to be 0.80 and 0.25, respectively for ligand atoms. Final scoring was performed on energy-minimized poses and displayed as Glide score. The best docked pose with lowest Glide score value was recorded for each ligand.

12.6—Results

Figure 27:
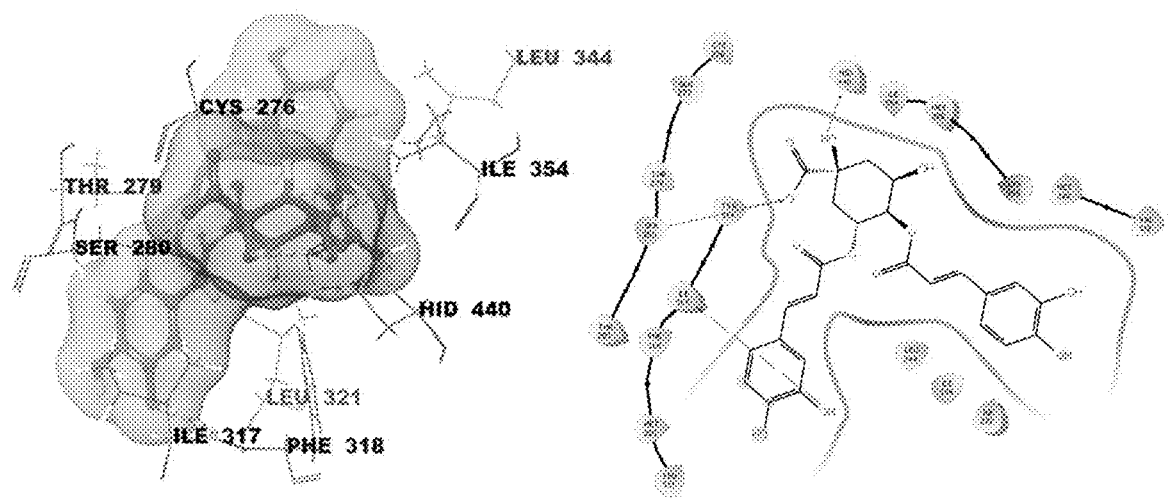
FIG. 27 shows the interaction of 3,4-di-O-caffeoyquinic acid with PPARα LBD.

The docking studies revealed strong interaction between the ligand binding site residues of PPARα LBD and the CGA isomers in the extract (Table 12). The glide score of the CGA isomers was found to be better than the original ligand TIPP703. The docking mode of 3,4-di-O-caffeoyquinic acid is shown in FIG. 27. The molecule interacted with key amino acid residues Tyr314, Ser280, His440. Further, 3-O-caffeoylquinic acid, 5-O-caffeoylquinic acid and 4,5-Di-O-caffeoylquinic acid shared common intermolecular H-bond interaction with Thr279.

TABLE 12

Docking score of CGA isomers of the extract and PPARα ligand binding domain

| Ligands | GScore | LipophilicEvdW | HBond | Interactions |
|---|---|---|---|---|
| 3-O-caffeoylquinic acid | −10.3 | −3.6 | −4.7 | Thr279, Tyr334, Leu331, Asn219, Cys276, His440 |
| 4-O-caffeoylquinic acid | −7.9 | −3.2 | −2.9 | Ile317, His440, Met320, Thr283 |
| 5-O-caffeoylquinic acid | −8.7 | −3.2 | −3.6 | Ser280, Thr279, His440, Asn219 |
| 3,4-Di-O-caffeoylquinic acid | −12.7 | −5.8 | −4.4 | Tyr314, Ser280, His440, Ile317 |
| 3,5-Di-O-caffeoylquinic acid | −13.3 | −5.5 | −5.8 | Asn219, Tyr314, Tyr334 |
| 4,5-Di-O-caffeoylquinic acid | −12.7 | −5.8 | −6.2 | Ile354, Thr283, Tyr314, Thr279, Cys276 |

Figure 28:
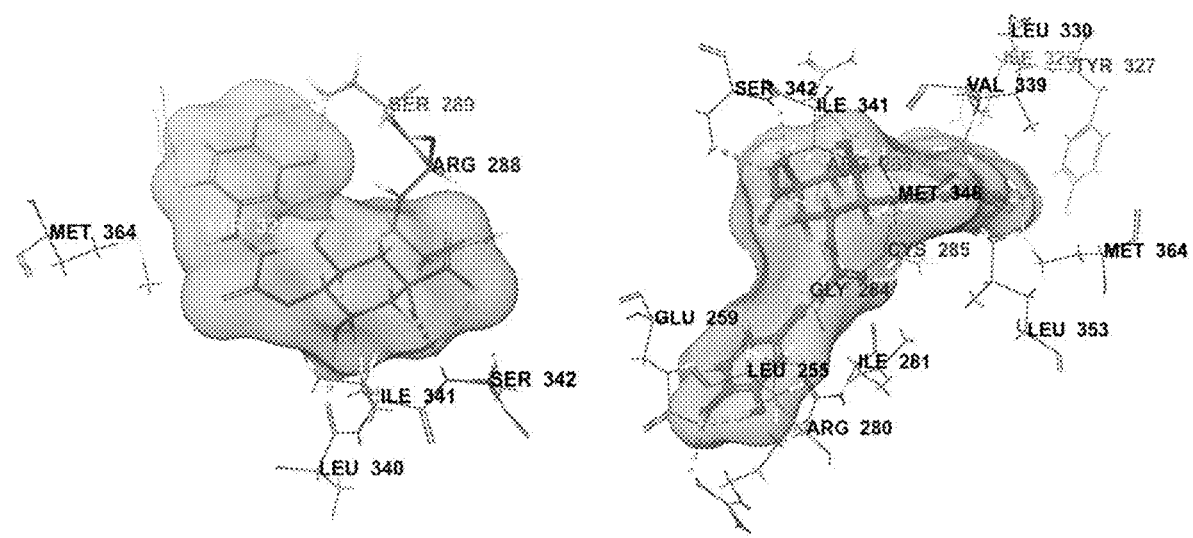
FIG. 28 shows ligand-PPARγ interactions of the best docking poses of (A) 4-O-caffeoylquinic acid, and (B) 3,4-Di-O-caffeoylquinic acid.

The docking simulation study was further extended to identify the receptor-binding potential of CGA isomers into the LBD of PPARγ (Table 13). Molecules such as 4-O-caffeoylquinic acid, 3,4-Di-O-caffeoylquinic acid, 3,5-Di-O-caffeoylquinic acid and 4,5-Di-O-caffeoylquinic acid made strong H-bond interactions with Ser342 which is a characteristic binding mode of the PPARγ partial agonists. The chlorogenic acids were predicted to have several hydrophobic interactions with Ala392, Leu330, Ile341, Leu333, Met364 and Ile281 from arm II and III of the PPARγ LBD. Further 3,5-Di-O-caffeoylquinic acid and 4,5-Di-O-caffeoylquinic acid had acidic amino acid Glu272 and 343 respectively. The best fit pose of 4-O-caffeoylquinic acid and 3,5-Di-O-caffeoylquinic acid are shown in FIG. 28.

is important for stabilizing the conformation of AF2-helix of LBD (Michalik et al. 2007; Yue et al. 2005; Ji and Zhang, 2008).

Further, the isomers of CGA in the extract were screened for their interaction with the LBD of PPARγ in order to determine their role as full/partial agonists. A comparative docking study of CGA isomers and a set of full and partial agonists with the LBD of PPARγ was conducted. It was interesting to find that chlorogenic acids showed strong binding affinity with the ligand binding domain of PPARγ. Previously the LBD of PPARγ has been identified on the basis of its interaction with endogenous ligands such as fatty acids and lipid metabolites (Waku et al. 2009). PPARγ full agonists bind to the H12 helix of the LBD leading to

TABLE 13

Docking simulation of CGA isomers of the extract and PPARγ ligand binding domain

| Ligands | GScore | LipophilicEvdW | HBond | Interactions |
|---|---|---|---|---|
| 3-O-caffeoylquinic acid | −10.2 | −3.5 | −4.5 | Ser289, Tyr327, Gly286, Phe282 |
| 4-O-caffeoylquinic acid | −10.2 | −3.9 | −4.6 | Ser289, Ser342, Leu340 |
| 5-O-caffeoylquinic acid | −9.2 | −4.0 | −3.4 | Gly284, Ser289 |
| 3,4-Di-O-caffeoylquinic acid | −11.0 | −5.5 | −3.9 | Ser289, Ser342, Glu259 |
| 3,5-Di-O-caffeoylquinic acid | −12.3 | −5.0 | −4.7 | Tyr327, Ile281, Ser342, Glu272, Arg280 |
| 4,5-Di-O-caffeoylquinic acid | −9.0 | −3.9 | −4.3 | Cys285, Ser342, Glu343 |

12.7—Discussion

Search for PPARα/γ dual agonists in sources such as plants provide an alternative strategy to treat metabolic disorders such as dyslipidemia and insulin resistance. The extract is a rich source of polyphenols particularly chlorogenic acids. The rationale of the current study was to identify the PPARγ and PPARγ ligands in the extract.

The six isomers of chlorogenic acids in the extract were analyzed for interaction with the LBD of PPARγ. Fenofibrate, a fibrate drug for dyslipidemia is known to interact with Thr279 amino acid in the LBD of PPARγ (Park et al. 2013). Interestingly, 3-O-caffeoylquinic acid, 5-O-caffeoylquinic acid and 4,5-Di-O-caffeoylquinic acid in the extract showed H-bond interaction with Thr279. Further the intermolecular interactions of CGA isomers of the extract included Ser280, Tyr314 and His440. This H-bond network conformational change and activation of PPARγ (Zoete et al. 2007; Farce et al. 2009). However, partial agonists bind differently i.e., in a H12-independent manner attributing to the decreased transcriptional activation of PPARγ. Most of the partial agonists interact with the LBD through hydrogen bonding with Ser342 (Farce et al. 2009) and several hydrophobic interactions. Similar interactions were evident between the extract chlorogenic acids and PPARγ LBD. The isomers of CGA such as 4-O-caffeoylquinic acid, 3,4-di-O-caffeoylquinic acid, 3,5-di-O-caffeoylquinic acid and 4,5-di-O-caffeoylquinic acid were selective PPARγ modulators (SPPARγMs). These molecules in the extract act as partial agonists of PPARγ exhibiting characteristic different interactions than do full agonists (Guasch et al. 2011). Also it was found that there was no H-bonding of CGA isomers except 3-O-caffeoylquinic acid and 3,5-Di-O-caffeoylquinic acid, with residues Tyr327, His449, His323 and Tyr473 from arm I of PPARγ LBD. This could explain the PPARγ partial agonism of the CGA isomers in the extract.

REFERENCES

1. Balakumar P., Kathuria S. Submaximal PPARgamma activation and endothelial dysfunction: new perspectives for the management of cardiovascular disorders. Brit J Pharmacol. 2012; 166:1981-1992.
2. Berger J, Moller D E (2002) The mechanisms of action of PPARs. Annu Rev Med 53: 409-435.
3. Beutler J. A. Natural products as a foundation for drug discovery. Curr Protoc Pharmacol. 2009 Chapter 9:Unit 9 11.
4. Cornick C. L., Strongitharm B. H., Sassano G., Rawlins C., Mayes A. E., Joseph A. N. Identification of a novel agonist of peroxisome proliferator-activated receptors alpha and gamma that may contribute to the anti-diabetic activity of guggulipid in Lep(ob)/Lep(ob) mice. J Nutr Biochem. 2009; 20:806-815.
5. Cragg G. M., Newman D. J. Natural products: a continuing source of novel drug leads. Biochim Biophys Acta. 2013; 1830: 3670-3695.
6. Dang Z. C., Audinot V., Papapoulos S. E., Boutin J. A., Lowik C. W. Peroxisome proliferator-activated receptor gamma (PPARgamma) as a molecular target for the soy phytoestrogen genistein. J Biol Chem. 2003; 278: 962-967.
7. Fang F., Kang Z., Wong C. Vitamin E tocotrienols improve insulin sensitivity through activating peroxisome proliferator-activated receptors. Mol Nutr Food Res. 2010; 54:345-352.
8. Fang X. K., Gao J., Zhu D. N. Kaempferol and quercetin isolated from *Euonymus alatus* improve glucose uptake of 3T3-L1 cells without adipogenesis activity. Life Sci. 2008; 82:615-622.
9. Farce A, Renault N, Chavatte P (2009) Structural insight into PPARgamma ligands binding. Curr Med Chem 16: 1768-1789
10. Francis G A, Fayard E, Picard F, Auwerx J (2003) Nuclear receptors and the control of metabolism. Annu Rev Physiol 65: 261-311.
11. Gouthamchandra K, Sudeep H V, Venkatesh B J, Shyamprasad K. Chlorogenic acid complex (CGA7), standardized extract from green coffee beans exerts anticancer effects against cultured human colon cancer HCT-116 cells. Food Science and Human Wellness, 2017
12. Guasch L, Sala E, Valls C, Blay M, Mulero M, et al. (2011) Structural insights for the design of new PPAR-gamma partial agonists with high binding affinity and low transactivation activity. J Comput Aided Mol Des, 25: 717-728
13. Harmon G. S., Lam M. T. & Glass C. K. PPARs and lipid ligands in inflammation and metabolism. Chemical reviews 111, 6321-6340 (2011).
14. Heald M., Cawthorne M. A. Dual acting and pan-PPAR activators as potential anti-diabetic therapies. Handb Exp Pharmacol. 2011:35-51.
15. Higgins L. S., Depaoli A. M. Selective peroxisome proliferator-activated receptor gamma (PPARgamma) modulation as a strategy for safer therapeutic PPAR-gamma activation. Am J Clin Nut. 2010; 91:725-2675.
16. Ji C G, Zhang J Z (2008) Protein polarization is critical to stabilizing AF-2 and helix-2' domains in ligand binding to PPAR-gamma. J Am Chem Soc 130: 17129-17133.
17. Jo, S. H., Ha, K. S., Moon, K. S., Lee, O. H., Jang, H. D., & Kwon, Y. I. (2011). In vitro and in vivo anti-hyperglycemic effects of Omija (Schizandra chinensis) fruit. International Journal of Molecular Sciences, 12(2), 1359-1370. Kalyanker, P., Zhu, Z., O'Cuinn, G., & FitzG
18. Kahn S. E. et al. Rosiglitazone-associated fractures in type 2 diabetes: an Analysis from A Diabetes Outcome Progression Trial (ADOPT). Diabetes Care 31, 845-851 (2008).
19. Kwon, Y. I. I., Vattem, D. A., & Shetty, K. (2006). Evaluation of clonal herbs of Lamiaceae species for management of diabetes and hypertension. Asia Pacific Journal of Clinical Nutrition, 15(1), 107-118
20. Michalik L, Zoete V, Krey G, Grosdidier A, Gelman L, et al. (2007) Combined simulation and mutagenesis analyses reveal the involvement of key residues for peroxisome proliferator-activated receptor alpha helix 12 dynamic behavior. J Biol Chem 282: 9666-9677.
21. Park M H, Park J Y, Lee H J, Kim D H, Park D, Jeong H O, Park C H, Chun P, Moon H R, Chung H Y. (2013) Potent anti-diabetic effects of MHY908, a newly synthesized PPAR α/γ dual agonist in db/db mice. Plos one, 8(11), e78815.
22. Shearer B G, Billin A N (2007) The next generation of PPAR drugs: do we have the tools to find them? Biochim Biophys Acta 1771: 1082-1093.
23. Sudeep H V, Venkatakrishna K, Dipak Patel, Shyamprasad K. Biomechanism of chlorogenic acid complex mediated plasma free fatty acid metabolism in rat liver. BMC Complementary and Alternative medicine, 2016; 16: 274.
24. Takahashi N., Goto T., Taimatsu A., Egawa K., Katoh S., Kusudo T. Bixin regulates mRNA expression involved in adipogenesis and enhances insulin sensitivity in 3T3-L1 adipocytes through PPARgamma activation. Biochem Biophys Res Commun. 2009; 390:1372-1376.
25. Tenenbaum A., Fisman E. Z. Balanced pan-PPAR activator bezafibrate in combination with statin: comprehensive lipids control and diabetes prevention? Cardiovasc Diabetol. 2012; 11:140.
26. Waku T, Shiraki T, Oyama T, et al. Structural insight into PPARγ activation through covalent modification with endogenous fatty acids. Journal of Molecular Biology, 2009; 385(1): 188-199.
27. Willson™, Brown P J, Sternbach D D, Henke B R (2000) The PPARs: from orphan receptors to drug discovery. J Med Chem 43: 527-550.
28. Yue L, Ye F, Xu X, Shen J, Chen K, et al. (2005) The conserved residue Phe273(282) of PPARalpha(gamma), beyond the ligand-binding site, functions in binding affinity through solvation effect. Biochimie 87: 539-550.
29. Zieleniak A., Wojcik M. & Wozniak L. A. Structure and physiological functions of the human peroxisome proliferator-activated receptor gamma. Archivum immunologiae et therapiae experimentalis 56, 331-345 (2008).
30. Zoete V, Grosdidier A, Michielin O (2007) Peroxisome proliferator-activated receptor structures: ligand specificity, molecular switch and interactions with regulators. Biochim Biophys Acta 1771: 915-925

The invention claimed is:
1. A method for treating a metabolic disorder, comprising administering to a patient in need thereof sunflower seed extract comprising a mixture of chlorogenic acids, said mixture comprising 3-CQA; 5-CQA; 4-CQA; 3,4-diCQA; 3,5-diCQA; and 4,5-diCQA.
2. The method of claim 1, wherein said mixture comprises 4.1±1.42 w/w % 3-CQA, 28±4.65 w/w % 5-CQA, 6.5±2.25 w/w % 4-CQA, 0.84±0.26 w/w % 3,4-diCQA, 1.23±0.34 w/w % 3,5-diCQA, and 1.85±0.42 w/w % 4,5-diCQA.

3. The method of claim 1, wherein said extract has a total chlorogenic acid content of about 42 w/w %.

4. The method of claim 1, wherein said extract has a total chlorogenic acid content of 42.50±2.5 w/w %.

5. The method of claim 1, wherein said extract is *Helianthus annuus* seed extract.

6. The method of claim 1, wherein administering said extract reduces at least one of glucose, total lipid content, HDL cholesterol, LDL cholesterol, VLDL cholesterol, triglyceride, Lp(a), apoA-I, apoE, and non-esterified fatty acids in the blood of said patient.

7. The method of claim 1, wherein said metabolic disorder is selected from the group consisting of prediabetes, diabetes, obesity, dyslipidemia, hyperglycemia, and combinations thereof.

8. The method of claim 1, wherein said metabolic disorder is type 1 diabetes or type 2 diabetes.

9. The method of claim 1, wherein said extract is administered systemically.

10. The method of claim 1, wherein said extract is administered by a route selected from the group consisting of orally, buccally, sub-lingually, parenterally, intravenously, intravaginally, rectally, inhalation, and combinations thereof.

11. The method of claim 1, wherein said extract is administered orally.

12. The method of claim 1, wherein said extract is in a form selected from the group consisting of powder, liquid, pill, tablet, pellet, capsule, thin film, solution, spray, syrup, linctus, lozenge, pastille, chewing gum, paste, vapor, suspension, emulsion, ointment, cream, lotion, liniment, gel, drop, topical patch, buccal patch, bead, gummy, gel, sol, and injection.

13. The method of claim 1, wherein said extract further comprises a vitamin, mineral, extract, amino acid, carbohydrate, lipid, excipient, caffeine, flavoring, sweetener, preservative, or combinations thereof.

* * * * *